(12) United States Patent
Reigan et al.

(10) Patent No.: US 10,947,238 B2
(45) Date of Patent: Mar. 16, 2021

(54) WEE1 KINASE INHIBITORS AND METHODS OF MAKING AND USING THE SAME

(71) Applicant: THE REGENTS OF THE UNIVERSITY OF COLORADO, a body corporate, Denver, CO (US)

(72) Inventors: Philip Reigan, Denver, CO (US); Christopher Matheson, Denver, CO (US)

(73) Assignee: The Regents of the University of Colorado, A Body Corporate, Denver, CO (US)

(*) Notice: Subject to any disclaimer, the term of this patent is extended or adjusted under 35 U.S.C. 154(b) by 0 days.

(21) Appl. No.: 15/772,554

(22) PCT Filed: Nov. 1, 2016

(86) PCT No.: PCT/US2016/059948
§ 371 (c)(1),
(2) Date: May 1, 2018

(87) PCT Pub. No.: WO2017/072629
PCT Pub. Date: May 4, 2017

(65) Prior Publication Data
US 2019/0084985 A1    Mar. 21, 2019

Related U.S. Application Data

(60) Provisional application No. 62/249,329, filed on Nov. 1, 2015.

(51) Int. Cl.
| | |
|---|---|
| *C07D 487/02* | (2006.01) |
| *C07D 487/04* | (2006.01) |
| *A61K 31/519* | (2006.01) |
| *A61K 33/24* | (2019.01) |
| *A61K 31/5377* | (2006.01) |
| *A61P 35/02* | (2006.01) |
| *A61P 35/04* | (2006.01) |
| *A61K 31/7068* | (2006.01) |

(52) U.S. Cl.
CPC .......... *C07D 487/04* (2013.01); *A61K 31/519* (2013.01); *A61K 31/5377* (2013.01); *A61K 33/24* (2013.01); *A61P 35/02* (2018.01); *A61P 35/04* (2018.01); *A61K 31/7068* (2013.01)

(58) Field of Classification Search
CPC ............................ C07D 487/02; C07D 487/04
See application file for complete search history.

(56) References Cited

U.S. PATENT DOCUMENTS

| 7,834,019 B2 | 11/2010 | Sagara et al. | |
|---|---|---|---|
| 7,947,695 B2 | 5/2011 | Freyne et al. | |
| 2007/0254892 A1* | 11/2007 | Sagara | C07D 487/04 514/252.16 |
| 2010/0221211 A1 | 9/2010 | Furuyama et al. | |
| 2014/0303178 A1 | 10/2014 | Sagara et al. | |
| 2016/0031877 A1 | 2/2016 | Smaill et al. | |

FOREIGN PATENT DOCUMENTS

| WO | WO 2005/077954 | 8/2005 |
|---|---|---|
| WO | WO 2015/092431 | 6/2015 |
| WO | WO 2017/075629 A2 | 5/2017 |
| WO | WO 2019/169065 A2 | 9/2019 |

OTHER PUBLICATIONS

International Preliminary Report on Patentability for International (PCT) Patent Application No. PCT/US2016/059948, dated May 11, 2018, 7 pages.
Berge et al., "Pharmaceutical Salts," Journal of Pharmaceutical Sciences, vol. 66, No. 1, Jan. 1977, pp. 1-19.
Bridges et al., "MK-1775, a Novel Wee1 Kinase Inhibitor, Radiosensitizes p53-defective Human Tumor Cells," Clinical Cancer Research, vol. 17, No, 17, Sep. 2011, pp. 5638-5648.
Bucher et al., "G2 checkpoint abrogation and checkpoint kinase-1 targeting in the treatment of cancer," British Journal of Cancer, vol. 98, No. 3, Feb. 2008, pp. 523-528.
Chen et al., "Targeting the S and G2 checkpoint to treat cancer," Drug Discovery Today, vol. 17, No. 5-6, Mar. 2012, pp. 194-202.
De Witt Hamer et al., "WEE1 kinase targeting combined with DNA-damaging cancer therapy catalyzes mitotic catastrophe," Clinical Cancer Research, vol. 17, No. 13, Jul. 2011, pp. 4200-4207.

(Continued)

*Primary Examiner* — Bruck Kifle
(74) *Attorney, Agent, or Firm* — Cooley LLP; Ivor R. Elrifi; Matthew Pavao

(57) ABSTRACT

A compound, or a pharmaceutically acceptable salt thereof, having a chemical structure of formula (I) or formula (II), and methods of using these compounds to treat cancer in an individual.

13 Claims, 20 Drawing Sheets

(56) References Cited

OTHER PUBLICATIONS

Do et al., "Wee1 kinase as a target for cancer therapy," Cell Cycle, vol. 12, No. 19, Oct. 2013, pp. 3159-3164.
Forte et al., "Gene Expression Analysis of PTEN Positive Glioblastoma Stem Cells Identifies DUB3 and Wee1 Modulation in a Cell Differentiation Model," PLoS One, vol. 8, No. 12, 2013, 6 pages.
Hirai et al., "MK-1775, a small molecule Wee1 inhibitor, enhances antitumor efficacy of various DNA-damaging agents, including 5-fluorouracil," Cancer Biology & Therapy, vol. 9, No. 7, Apr. 2010, pp. 514-522.
Hirai et al., "Small-molecule inhibition of Wee1 kinase by MK-1775 selectively sensitizes p53-deficient tumor cells to DNA-damaging agents," Molecular Cancer Therapeutics, vol. 8, No. 11, Nov. 2009, pp. 2992-3000.
Igarashi et al., "Wee1 +-like gene in human cells," Nature, vol. 353, No. 6339, Sep. 1991, pp. 80-83.
Indovina et al., "Targeting the checkpoint kinase WEE1: Selective sensitization of cancer cells to DNA-damaging drugs," Cancer Biology & Therapy, vol. 9, No. 7, Apr. 2010, pp. 523-525.
Jin et al., "Role of inhibitory CDC2 phosphorylation in radiation-induced G2 arrest in human cells," Jounral of Cell Biology, vol. 134, No. 4, Aug. 1996, pp. 963-970.
Leijen et al., "Abrogation of the G2 Checkpoint by Inhibition of Wee-1 Kinase Results in Sensitization of p53-Deficient Tumor Cells to DNA-Damaging Agents," Current Clinical Pharmacology, vol. 5, No. 3, Aug. 2010, pp. 186-191. Abstract Only.
McGowan et al., "Human Wee1 kinase inhibits cell division by phosphorylating p34cdc2 exclusively on Tyr15," The EMBO Journal, vol. 12, No. 1, Jan. 1993, pp. 75-85.
Mir et al., "In Silico Analysis of Kinase Expression Identifies WEE1 as a Gatekeeper against Mitotic Catastrophe in Glioblastoma," Cancer Cell, vol. 18, No. 3, Sep. 2010, pp. 244-257.
Parker et al., "Inactivation of the p34cdc2-cyclin B complex by the human WEE1 tyrosine kinase," Science, vol. 257, No. 5078, Sep. 1992, pp. 1955-1957.

Svensson et al., "The design and bioactivation of presystemically stable prodrugs," Drug Metabolism Reviews, vol. 19, No. 2, 1988, pp. 165-194.
Syljuåsen et al., "Targeting lung cancer through inhibition of checkpoint kinases," Frontiers in Genetics, vol. 6, No. 70, 11 pages, (2015).
Tuel-Ahlgren et al., "Role of tyrosine phosphorylation in radiation-induced cell cycle-arrest of leukemic B-cell precursors at the G2-M transition checkpoint," Leukemia & Lymphoma, vol. 20, No. 5-6, Feb. 1996, pp. 417-426.
Wang et al., "Global Profiling of Signaling Networks: Study of Breast Cancer Stem Cells and Potential Regulation," The Oncologist, vol. 16, No. 7, Jul. 2011, pp. 966-979.
Zhou et al., "A regimen combining the Wee1 inhibitor AZD1775 with HDAC inhibitors targets human acute myeloid leukemia cells harboring various genetic mutations," Leukemia, vol. 29, No. 4, Apr. 2015, pp. 807-818.
International Search Report issued by the U.S. Patent and Trademark Office for International Patent Application No. PCT/US2016/059948, dated Apr. 12, 2017, 5 pages.
Written Opinion issued by the U.S. Patent and Trademark Office for International Patent Application No. PCT/US2016/059948, dated Apr. 12, 2017, 5 pages.
Van Linden, Annemie A. et al., "Inhibition of Wee1 Sensitizes Cancer Cells to Antimetabolite Chemotherapeutics in Vitro and in Vivo, Independent of p53 Functionality", Mol Cancer Ther; vol. 12 No. 12, Dec. 2013, pp. 2675-2684.
O'Connor, L.J. et al., "Efficient synthesis of 2-nitroimidazole derivatives and the bioreductive clinical candidate Evofosfamide (TH-302)", Organic Chemistry Frontiers 2, (2015), p. 1026-1029.
Tanabe, K. et al., "Current molecular design of intelligent drugs and imaging probes targeting tumor-specific microenvironments", Organic & Biomolecular Chemistry, 2008, p. 1-16.
Tercel, M et al., "Hypoxia-Selective Antitumor Agents. 16. Nitroarylmethyl Quaternary Salts as Bioreductive Prodrugs of the Alkylating Agent Mechlorethamine", Journal of Medicinal Chemistry, 2001, vol. 44, No. 21, p. 3511-3522.

* cited by examiner

|  | R | R' | WEE1; IC$_{50}$ (nM) |
|---|---|---|---|
| 11a | C(CH$_3$)$_2$OH | N(CH$_3$)$_2$ | 42.8 ± 22 |
| 11b | C(CH$_3$)$_2$OH | N(C$_5$H$_{10}$) | 33.3 ± 20 |
| 11c | C(CH$_3$)$_2$OH | N(CH$_2$CH$_2$)$_2$O | 37.8 ± 6 |
| AZD1775 | C(CH$_3$)$_2$OH | N(CH$_2$CH$_2$)$_2$NCH$_3$ | 18.7 ± 8 |
| 11d | C(CH$_3$)$_2$OH | N(CH$_2$CH$_2$)$_2$NCO$_2$CH$_3$ | 27.8 ± 15 |
| 11e | CF$_3$ | N(CH$_3$)$_2$ | 1121 ± 236 |
| 11f | CF$_3$ | N(C$_5$H$_{10}$) | 574 ± 340 |
| 11g | CF$_3$ | N(CH$_2$CH$_2$)$_2$O | 561 ± 300 |
| 11h | CF$_3$ | N(CH$_2$CH$_2$)$_2$NCH$_3$ | 112 ± 24 |
| 11i | CF$_3$ | N(CH$_2$CH$_2$)$_2$NCO$_2$CH$_3$ | 681 ± 93 |
| 11j | OCH$_3$ | N(CH$_3$)$_2$ | 255 ± 11 |
| 11k | OCH$_3$ | N(C$_5$H$_{10}$) | 147 ± 18 |
| 11l | OCH$_3$ | N(CH$_2$CH$_2$)$_2$O | 104 ± 35 |
| 11m | OCH$_3$ | N(CH$_2$CH$_2$)$_2$NCH$_3$ | 30.5 ± 8 |
| 11n | OCH$_3$ | N(CH$_2$CH$_2$)$_2$NCO$_2$CH$_3$ | 157 ± 26 |

Figure 5B

AZD1775 (nM)

| Cisplatin (nM) | 37.5 | 75 | 150 | 300 | 600 |
|---|---|---|---|---|---|
| 150 | 13.47 | 3.06 | 1.39 | 0.97 | 0.87 |
| 300 | 6.50 | 2.67 | 0.87 | 0.91 | 0.83 |
| 600 | 2.32 | 1.02 | 0.77 | 0.85 | 0.90 |
| 1200 | 0.80 | 0.66 | 0.55 | 0.70 | 0.74 |
| 2400 | 0.42 | 0.37 | 0.39 | 0.55 | 0.65 |

11a (nM)

| Cisplatin (nM) | 37.5 | 75 | 150 | 300 | 600 |
|---|---|---|---|---|---|
| 150 | 1.13 | 1.65 | 2.13 | 2.73 | 1.94 |
| 300 | 2.08 | 2.43 | 3.90 | 2.34 | 1.49 |
| 600 | 1.15 | 1.11 | 1.02 | 1.07 | 1.37 |
| 1200 | 0.86 | 0.80 | 0.88 | 0.86 | 1.08 |
| 2400 | 0.71 | 0.71 | 0.63 | 0.58 | 0.50 |

11b (nM)

| Cisplatin (nM) | 37.5 | 75 | 150 | 300 | 600 |
|---|---|---|---|---|---|
| 150 | 1.84 | 1.54 | 1.80 | 1.80 | 2.01 |
| 300 | 3.16 | 3.45 | 3.97 | 3.01 | 1.24 |
| 600 | 1.25 | 1.41 | 1.12 | 0.81 | 0.89 |
| 1200 | 0.81 | 0.74 | 0.61 | 0.62 | 0.64 |
| 2400 | 0.66 | 0.55 | 0.48 | 0.33 | 0.18 |

11c (nM)

| Cisplatin (nM) | 37.5 | 75 | 150 | 300 | 600 |
|---|---|---|---|---|---|
| 150 | 1.04 | 1.98 | 69.75 | 4.64 | 1.01 |
| 300 | 1.50 | 2.84 | 6.02 | 2.26 | 0.73 |
| 600 | 1.48 | 1.91 | 1.46 | 0.94 | 0.67 |
| 1200 | 0.85 | 0.76 | 0.71 | 0.58 | 0.41 |
| 2400 | 0.61 | 0.43 | 0.32 | 0.22 | 0.03 |

11d (nM)

| Cisplatin (nM) | 37.5 | 75 | 150 | 300 | 600 |
|---|---|---|---|---|---|
| 150 | 1.68 | 2.38 | 1.76 | 1.64 | 0.86 |
| 300 | 2.89 | 3.64 | 1.98 | 0.96 | 0.79 |
| 600 | 0.99 | 0.96 | 0.66 | 0.69 | 0.76 |
| 1200 | 0.65 | 0.57 | 0.56 | 0.54 | 0.55 |
| 2400 | 0.61 | 0.50 | 0.36 | 0.27 | 0.23 |

11m (nM)

| Cisplatin (nM) | 37.5 | 75 | 150 | 300 | 600 |
|---|---|---|---|---|---|
| 150 | 1.34 | 2.82 | 1.96 | 1.15 | 0.57 |
| 300 | 3.00 | 4.25 | 3.02 | 0.66 | 0.42 |
| 600 | 1.06 | 0.97 | 0.53 | 0.36 | 0.42 |
| 1200 | 0.73 | 0.58 | 0.41 | 0.26 | 0.26 |
| 2400 | 0.61 | 0.48 | 0.23 | 0.11 | 0.03 |

Figure 12B

WEE1 KINASE INHIBITORS AND METHODS OF MAKING AND USING THE SAME

CROSS REFERENCE TO RELATED APPLICATIONS

This application is a national stage application under 35 U.S.C. 371 of PCT Application No. PCT/US2016/059948, having an international filing date of Nov. 1, 2016, which designated the United States, which PCT application claimed the benefit of U.S. Provisional Patent Application Ser. No. 62/249,329, filed on Nov. 1, 2015, both of which are incorporated herein by reference.

GOVERNMENT INTEREST

This invention was made with Government support under grant number R21NS084084 awarded by the National Institutes of Health (NIH). The U.S. Government has certain rights in this invention.

TECHNICAL FIELD

The invention relates to improvements in cancer chemotherapy.

BACKGROUND OF DISCLOSURE

Cell cycle checkpoints are surveillance mechanisms that monitor and coordinate the order and fidelity of cell cycle events. When defects in the division program of a cell are detected, checkpoints prevent the pursuant cell cycle transition through regulation of the relevant cyclin-cdk complexes. Checkpoints that respond to DNA damage have been described for the G1, S and G2 phases of the cell cycle. For example, the p53 tumor suppressor is a key regulator of G1/S checkpoints, and can promote cell cycle delay or apoptosis in response to DNA damage. Cancer cells that possess a deficient G1 checkpoint, which impairs the ability of the cell to halt the cell cycle in order to repair DNA damage prior to replication, gives these cancer cells a means to accumulate mutations and propagate irregularities that are favorable to cancer formation. These cancer cells are therefore reliant on the G2 checkpoint to prevent excessive DNA damage that leads to apoptosis via mitotic catastrophe (Chen T, et al. Drug Discovery Today. 2012; 17(5-6):194-202; Bucher N, et al., British Journal of Cancer. 2008; 98(3):523-8). In normal cells, the G1 checkpoint is not compromised; therefore, the G2 checkpoint is not burdened with halting the cell cycle prior to DNA damage repair. Thus, modulation of the G2 checkpoint selectively impacts tumorigenesis rather than normal cell growth.

Wee1 is a tyrosine kinase that is a critical component of the ataxia-telangiectasia-mutated-and-Rad3-related (ATR)-mediated G2 cell cycle checkpoint control that prevents entry into mitosis in response to cellular DNA damage (Do K, et al., Cell Cycle. 2013; 12(19):3159-64). ATR phosphorylates and activates CHK1, which in turn activates Wee1, leading to the selective phosphorylation of cyclin-dependent kinase 1 (CDK1) at Tyr5 (Parker L L, et al., Science. 1992; 257(5078):1955-7; McGowan C H, et al., The EMBO Journal. 1993; 12(1):75-85), thereby stabilizing the CDK1-cyclin B complex and halting cell-cycle progression (Indovina P, et al., Cancer Biol. Ther. 9(7):523-5; Jin P, et al., J Cell Biol. 1996; 134(4):963-70). This process confers a survival advantage by allowing tumor cells time to repair damaged DNA prior to entering mitosis (Igarashi M, et al., 1991; 353(6339):80-3). Inhibition of Wee1 abrogates the G2 checkpoint, forcing cancer cells with DNA damage to enter into unscheduled mitosis and undergo cell death via mitotic catastrophe (De Witt Hamer P C, et al., Clin Cancer Res. 2011; 17(13):4200-7; Hirai H, et al., Mol Cancer Ther. 2009; 8(11):2992-3000; Hirai H, et al., 2010; 9(7):514-22; Indovina P, et al., Cancer biology & therapy. 2010; 9(7): 523-5; Leijen S, et al. Current clinical pharmacology. 2010; 5(3):186-91. Mir S E, et al., Cancer Cell. 2010; 18(3):244-57; Bridges K A, et al., Clinical cancer research 2011; 17(17):5638-48).

SUMMARY

One aspect of this disclosure provides a compound, or a pharmaceutically acceptable salt thereof, having a chemical structure of formula (I) or formula (II):

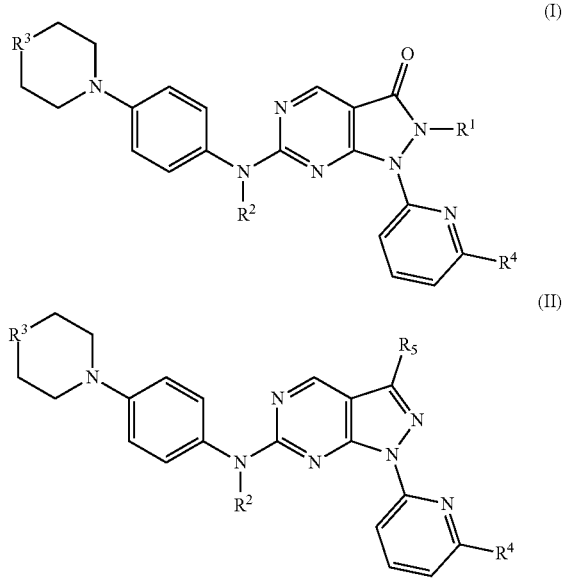

wherein:

$R^1$ is H, $C_{1-6}$ alkyl, $C_{2-6}$ alkenyl, substituted $C_{1-6}$ alkyl, or substituted $C_{2-6}$ alkenyl; $R^2$ is H, aryl, substituted aryl, heteroaryl, substituted heteroaryl, $C_{1-6}$ alkyl, or substituted $C_{1-6}$ alkyl;

$R^3$ is methylene, oxygen, amine, or nitrogen substituted with $C_{2-6}$ alkyl substituted $C_{1-6}$ alkyl, $C_{1-6}$ alkoxy, or $CO_2R^6$, but where $R^3$ cannot be N-methyl; and, $R^4$ is H, or an optionally substituted alkyl ($C_{1-6}$);

$R^5$ is H, $C_{1-6}$ alkyl, substituted $C_{1-6}$ alkyl, $C_{2-6}$ alkenyl, $C_{1-6}$ alkoxy, aryl, substituted aryl, heteroaryl, substituted heteroaryl, $OR^6$, $SR^6$, $CO_2R^6$, $OC(=O)R^6$, or $NR^7R^8$;

$R^6$ is H, $C_{1-6}$ alkyl, substituted $C_{1-6}$ alkyl, $C_{3-8}$ cycloalkyl, aryl, substituted aryl, heteroaryl or substituted heteroaryl; and, $R^7$ and $R^8$ are independently H, $C_{1-6}$ alkyl, substituted $C_{1-6}$ alkyl, $C_{3-8}$ cycloalkyl, $C_{2-4}$ alkenyl, aryl, substituted aryl, heteroaryl or substituted heteroaryl.

$R^7$ and $R^8$ may independently be H, $C_{1-6}$ alkyl, $C_{3-8}$ cycloalkyl, $C_{2-4}$ alkenyl, aryl, heteroaryl, or $C_{1-6}$ alkyl substituted with hydroxy, mercapto, amino, sulfonic acid, carboxylic acid, halide, $C_{1-6}$ alkyl, $C_{1-6}$ alkenyl, $C_{1-4}$ alkoxy, $OR^9$, $SR^9$, $NR^9R^9$, $CO_2R^9$, $OC(=O)R^9$, heteroaryl, or combinations thereof; and, $R^9$ may be H, or $C_{1-6}$ alkyl, $C_{3-8}$ cycloalkyl, $C_{2-4}$ alkenyl, aryl, heteroaryl, or $C_{1-6}$ alkyl substituted with hydroxy, mercapto, amino, sulfonic acid, carboxylic acid, halide, $C_{1-6}$ alkyl, $C_{1-6}$ alkenyl, $C_{1-4}$ alkoxy.

$R^1$ may be $C_{1-6}$ alkyl substituted with hydroxy, mercapto, amino, sulfonic acid, carboxylic acid, halide, $C_{1-6}$ alkyl, $C_{1-4}$ alkoxy, $OR^6$, $SR^6$, $NR^7R^8$, $CO_2R^6$, $OC(=O)R^6$, heteroaryl, or combinations thereof.

$R^2$ may be $C_{1-6}$ alkyl substituted with hydroxy, mercapto, amino, sulfonic acid, carboxylic acid, halide, $C_{1-6}$ alkyl, $C_{1-4}$ alkoxy, $OR^6$, $SR^6$, $NR^7R^8$, $CO_2R^6$, $OC(=O)R^6$, heteroaryl, or combinations thereof.

$R^3$ may be methylene, amine, of N substituted with $C_{1-6}$ alkyl substituted with hydroxy, mercapto, amino, sulfonic acid, carboxylic acid, halide, $C_{1-6}$ alkyl, $C_{1-4}$ alkoxy, $OR^6$, $SR^6$, $NR^7R^8$, $CO_2R^6$, $OC(=O)R^6$, heteroaryl, or combinations thereof, but not N-methyl.

$R^4$ may be $C_{1-6}$ alkyl substituted with hydroxy, mercapto, amino, sulfonic acid, carboxylic acid, halide, $C_{1-6}$ alkyl, $C_{1-4}$ alkoxy, $OR^6$, $SR^6$, $NR^7R^8$, $CO_2R^6$, $OC(=O)R^6$, heteroaryl, or combinations thereof.

$R^5$ may be $C_{1-6}$ alkyl substituted with hydroxy, mercapto, amino, sulfonic acid, carboxylic acid, halide, $C_{1-6}$ alkyl, $C_{1-4}$ alkoxy, $OR^6$, $SR^6$, $NR^7R^8$, $CO_2R^6$, $OC(=O)R^6$, heteroaryl, or combinations thereof.

Each of $R^1$, $R^2$, $R^4$, and $R^5$ may be hydrogen. Each of $R^1$, $R^2$, $R^4$, and $R^5$ may also be hydrogen, when $R^3$ is $CH_2$.

Another aspect of this disclosure provides pharmaceutical compositions comprising a Wee1 inhibitor compound of this disclosure and at least one pharmaceutically acceptable additive.

Another aspect of this disclosure provides pharmaceutical kits containing a pharmaceutical composition of this disclosure, prescribing information for the composition, and a container.

Another aspect of this disclosure provides methods for inhibiting Wee1 kinase activity in a subject, including administering to the subject a therapeutically effective amount of a Wee1 inhibitor compound of this disclosure, or a pharmaceutically acceptable salt thereof.

This disclosure also provides methods of preventing, treating, or ameliorating cancer, or preventing metastasis of a cancer in a subject, including administering a therapeutically-effective amount of a compound of this disclosure that inhibits Wee1 kinase to a subject in need thereof.

In these methods, the cancer may be an advanced solid tumor, a blood cancer (including, for example, acute myeloid leukemia), a brain tumor, an ovarian tumor, cervical cancer, squamous cell cancer of the head and neck, pancreatic cancer, and lung cancer.

In these methods, the Wee1 inhibitor compound may be administered to the subject within a pharmaceutical composition. The pharmaceutical composition may be a monophasic pharmaceutical composition suitable for parenteral or oral administration consisting essentially of a therapeutically-effective amount of the compound, and a pharmaceutically acceptable additive.

In these methods, the pharmaceutical composition may be administered in combination with one or more DNA-targeted agents, including DNA alkylating agents and topoisomerase inhibitors, including cisplatin, capecitabine, carboplatin, cyclophosphamide, cytarabine, dauoribicin, docetaxel, doxorubicin, 5-fluorouracil, gemcitabine, methotrexate, paclitaxel, premetrexed, irinotecan temozolomide, topotecan, radiation, or combinations thereof.

In these methods, the pharmaceutical composition may be administered in combination with at least one of cisplatin, cytarabine, or temozolomide.

In related aspects, this disclosure also provides the use of a Wee1 inhibitor compound of this disclosure, or a pharmaceutically acceptable salt thereof, in the manufacture of a medicament for the treatment of cancer. Similarly, this disclosure provides a Wee1 inhibitor compound of this disclosure, or a pharmaceutically acceptable salt thereof, for use in the treatment of cancer.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become readily apparent from the Description of Embodiments, particularly when taken together with the drawings.

BRIEF DESCRIPTION OF DRAWINGS

FIG. 1A is a gene expression heat map of 50 dysregulated cell cycle-related kinases in 16 medulloblastoma tissue samples compared with 3 normal cerebellum. FIG. 1B is a dot plot of the average Z score of 3 separate siRNAs targeting a single kinase of the 710 human kinase genes targeted in the siRNA screen. Each dot represents the average Z score. FIG. 1C is a model of G2-M kinases that mediate Daoy cell proliferation. Kinases in red were statistically significant hits from the combined gene expression analysis and kinome-wide RNAi screen.

FIG. 2A shows a microarray analysis of Wee1 mRNA expression in pediatric medulloblastoma (Medullo), primitive neuroectodermal tumors (PNET), glioblastoma (GBM) and pilocytic astrocytoma (PA) compared with normal brain. FIG. 2B shows a microarray analysis of Wee1 mRNA expression in 90 medulloblastoma tissue samples compared with normal cerebellum. FIG. 2C shows that Wee1 protein levels are increased in 6 medulloblastoma cell lines, UPN514 and UPN605 are normal pediatric cerebellum (CB) lysates.

FIG. 3A shows Daoy and UW228 cells transfected with siRNA targeting WEE1 (siWEE1) or a non-silencing siRNA (siRNA N.C.) and real-time cell proliferation monitored using the xCELLigence system. FIG. 3B shows the effect of siWEE1 and siRNA N.C. on relative colony number.

FIGS. 5A and 5B depict the synthesis of AZD1775 analogs and their Wee1 inhibitory activity. FIG. 5A depicts the synthetic scheme for AZD1775 analogs 11a-11n. FIG. 5B shows Wee1 inhibitory activity of AZD1775 analogs in an in vitro kinase assay.

FIG. 6A shows in vitro inhibition of Wee1 kinase activity by AZD1775 and 11a-11n. FIG. 6B shows inhibitory IC50 curves for Wee1 inhibitors 11a-11d, 11m, and AZD1775. Emission ratios (665/615 nm) were determined for each inhibitor concentration in triplicate, and the data analyzed using a non-linear regression analysis of the log dose-response curve to give IC50 values.

FIG. 7A shows the structure of AZD1775 and 11d highlighting areas for structural modification. FIG. 7B shows the relationship between BBB permeability and the octanol/water partition coefficient for chemotherapeutic drugs taken from Neuwelt et al., for reference. Predicted BBB penetration for AZD1775 and 11d has been calculated using Quikprop and plots added to the graphic. Ready brain uptake (red) and limited brain uptake (green) areas.

FIG. 8A shows Daoy cell growth rate represented as 1/Slope (Δ cell index/hr) derived from a real-time cell proliferation assay (xCELLigence) between 4-56 hours following treatment with 75 nM (blue) and 150 nM (red) compounds 11a-11n and AZD1775, compared with DMSO (green). All values $P<0.001$ compared with DMSO. FIG. 8B shows the dose-response by MTS assay for Daoy cells treated with Wee1 inhibitor for 72 hours. AZD1775 (red) decreased the cellular viability of Daoy cells with an EC50 of 219±26 nM. All other inhibitors showed an effect at the maximum concentration (600 nM). FIG. 8C shows a dose-response by MTS assay for ONS-76 cells treated with AZD1775 (red) and 11d (blue) and 11m (green) for 72 hours. FIG. 8D shows D458 cell viability and total cell number determined by flow cytometry (Viacount) when exposed to increasing concentrations of AZD1775 (orange), 11d (blue) and 11m (green) for 72 hours. (Compared with DMSO, total cell number; $P<0.05=*$, $P<0.01=$, $P<0.001=*$. Non-viable cell number; $P<0.05=+$, $P<0.01=++$, $P<0.001=+++$).

FIG. 9A shows immunoblotting analysis of Daoy cell lysates treated with Wee1 inhibitors and DMSO control for 24 hours. Membranes were probed for pCDK1(Y15), total CDK1 and actin as a loading control. FIG. 9B shows quantitative ELISA determination of relative pCDK1 (Tyr5) levels in Daoy cell lysates (0.15 mg/ml total protein) treated with increasing concentrations of AZD1775 (red), 11d (blue) and 11m (green) for 24 hours. Interpolation of curves reveals that 125 nM AZD1775, 205 nM 11d and 565 nM 11m are required to reduce cellular pCDK1 (Tyr5) to the same level.

FIG. 10D is a plot of Daoy cell growth rates represented by 1/Slope (Δ cell index/hr) for AZD1775 (red), 11d (green) and 11m (blue) across a range of inhibitor concentrations. Growth rates were determined for the linear growth phase (t=30-80 hrs). Interpolation of data reveals growth rates at fixed inhibitor concentrations; 125 nM AZD1775, 1/Slope=0.033 Δ cell index/hr; 205 nM 11d, 1/Slope=0.063 Δ cell index/hr; 565 nM 11m, 1/Slope=0.012 Δ cell index/hr.

FIG. 11A shows the 0.1 μM compound addition, 0.5 μM compound addition (FIG. 11B), 1.0 μM compound addition (FIG. 11C), 3.01 μM compound addition (FIG. 11D). FIG. 11E shows the compound concentration, as determined by LC-MS/MS, in Daoy cell lysate over increasing concentrations of AZD1775, 11d and 11m incubated for 60 minutes prior to media aspiration and washing.

FIGS. 12A and 12B shows that Wee1 Inhibitors potentiate the activity of cisplatin at a non-toxic concentration. FIG. 12A shows a Combination Index (CI) plots generated using an MTS assay in Daoy cells treated with Wee1 inhibitor and cisplatin combinations for 72 hours. CI values determined using the Chou-Talalay equation, with combination treatments indicated as non-synergistic (red, >1.05), synergistic (green, <0.95) and intermediate (yellow, 0.96-1.04). FIG. 12B shows a numerical representation of CI plots.

FIG. 13A shows AZD1775 (20 mg/kg), and FIG. 13B shows AZD1775 (40 mg/kg) in nude mice 3 h after a single oral dose of drug. Data represent the mean±SD of 3 mice.

DESCRIPTION OF EMBODIMENTS

Figure 1A:
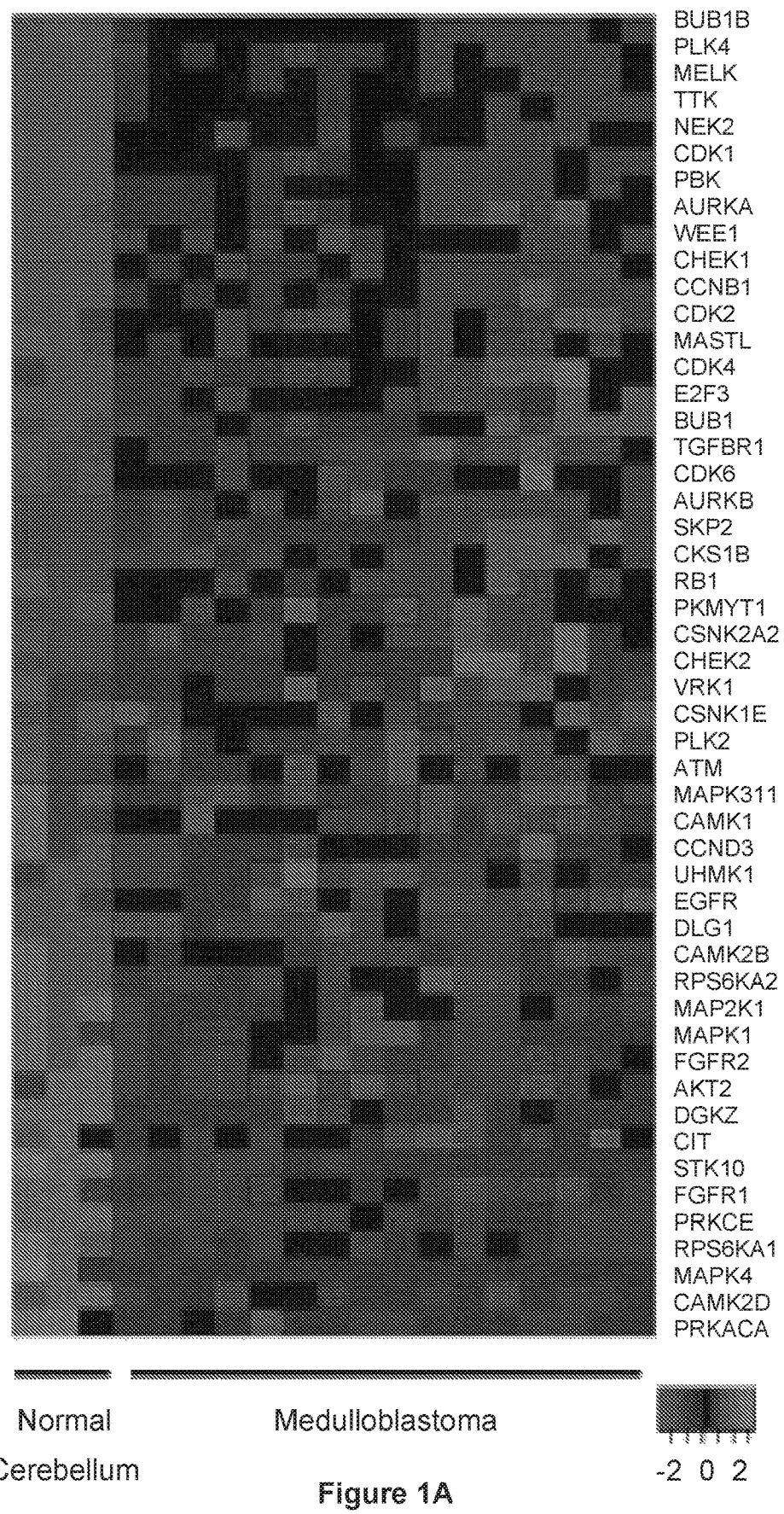
FIGS. 1A-1C show an analysis of kinases in medulloblastoma.

The present disclosure is drawn to Wee1 kinase inhibitors with significantly improved specificity for Wee1 kinase inhibition that demonstrate low cytotoxicity, good blood-brain barrier penetration, and synergy with cisplatin in the treatment of patients with advanced solid tumors or blood cancers.

To facilitate an understanding of the embodiments presented, the following explanations are provided.

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

"Administration of" and "administering a" compound or agent should be understood to mean providing a compound or agent, a prodrug of a compound or agent, or a pharmaceutical composition as described herein. The compound, agent or composition can be administered by another person to the subject (e.g., intravenously) or it can be self-administered by the subject (e.g., tablets or capsules).

The term "subject" refers to animals, including mammals (for example, humans and veterinary animals such as dogs, cats, pigs, horses, sheep, and cattle).

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, and aryl groups.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato, or other R-groups.

"Acyl" refers to a group having the structure RCO—, where R may be alkyl, or substituted alkyl. "Lower acyl" groups are those that contain one to six carbon atoms.

"Acyloxy refers to a group having the structure RCOO—, where R may be alkyl or substituted alkyl. "Lower acyloxy" groups contain one to six carbon atoms.

"Alkenyl" refers to a cyclic, branched or straight chain group containing only carbon and hydrogen, and unless otherwise mentioned typically contains one to twelve carbon atoms, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$ alkanoyl can be acetyl, propanoyl or butanoyl; halo$(C_1-C_6)$ alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$ alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "halogen" refers to fluoro, bromo, chloro, and iodo substituents.

"Aryl" refers to a monovalent unsaturated aromatic carbocyclic group having a single ring (e.g., phenyl) or multiple condensed rings (e.g., naphthyl or anthryl), which can optionally be unsubstituted or substituted.

The term "amino" refers to an R-group having the structure —$NH_2$, which can be optionally substituted with, for example, lower alkyl groups, to yield an amino group having the general structure —NHR or —$NR_2$.

"Nitro" refers to an R-group having the structure —$NO_2$.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aryl groups, pyridyl groups and furan groups are examples of aromatic groups. The conjugated system of an aromatic group contains a characteristic number of electrons, for example, 6 or 10 electrons that occupy the electronic orbitals making up the conjugated system, which are typically unhybridized p-orbitals.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid, and the like.

"Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine, and the like.

Some of the compounds described herein may also exist in their tautomeric form.

A "therapeutically effective amount" of the disclosed compounds is a dosage of the compound that is sufficient to achieve a desired therapeutic effect, such as inhibition of angiogenesis or an anti-tumor or anti-metastatic effect, inhibition of TNF-α activity, inhibition of immune cytokines, or treatment of a neurodegenerative disease. In some examples, a therapeutically effective amount is an amount sufficient to achieve tissue concentrations at the site of action that are similar to those that are shown to modulate angiogenesis, TNF-α activity, or immune cytokines, in tissue culture, in vitro, or in vivo. For example, a therapeutically effective amount of a compound may be such that the subject receives a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day.

The term "stereoisomer" refers to a molecule that is an enantiomer, diasteromer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

The term "modulate" refers to the ability of a disclosed compound to alter the amount, degree, or rate of a biological function, the progression of a disease, or amelioration of a condition. For example, modulating can refer to the ability of a compound to elicit an increase or decrease in angiogenesis, to inhibit TNF-α activity, or to inhibit tumor metastasis or tumorigenesis.

The term "angiogenic activity" refers to the ability of a disclosed compound or a particular concentration of a disclosed compound to stimulate angiogenesis. Angiogenic activity may be detected in vivo or in vitro. Angiogenic compounds or angiogenic concentrations of disclosed compounds stimulate angiogenesis, and such compounds and/or concentrations may be readily identified by those of ordinary skill in the art, using, for example, the methods described in the Examples that follow.

The term "anti-angiogenic activity" refers to the ability of a compound or a particular concentration of a disclosed compound to inhibit angiogenesis. Anti-angiogenic activity may be detected in vivo or in vitro. Anti-angiogenic or anti-angiogenic concentrations of disclosed compounds inhibit angiogenesis, and such compounds and/or concentrations may be readily identified by those of ordinary skill in the art, using, for example, the methods described in the Examples that follow.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactically administering a composition to a subject who does not exhibit signs of a disease or exhibits only early signs of the disease, for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999. In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers. Thus, these compounds can exist in different stereoisomeric forms. Accordingly, compounds and compositions may be provided as individual pure enantiomers or as stereoisomeric mixtures, including racemic mixtures. The compounds disclosed herein may be synthesized in, or are purified to be in, substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In exemplary embodiments, a substituted group is not substituted with another substituted group (e.g. substituted alkyl is substituted with unsubstituted aryl).

Overview of Particularly Disclosed Embodiments

Disclosed are compounds that inhibit Wee1 kinase enzymes with significantly improved specificity for Wee1 kinase and can therefore be used to treat a wide variety of advanced solid tumors and blood cancers. Pharmaceutically acceptable salts, stereoisomers, and metabolites of all the disclosed compounds also are contemplated.

An aspect of this disclosure provides compounds, or pharmaceutically acceptable salts thereof, having a chemical structure of formula (I) or formula (II):

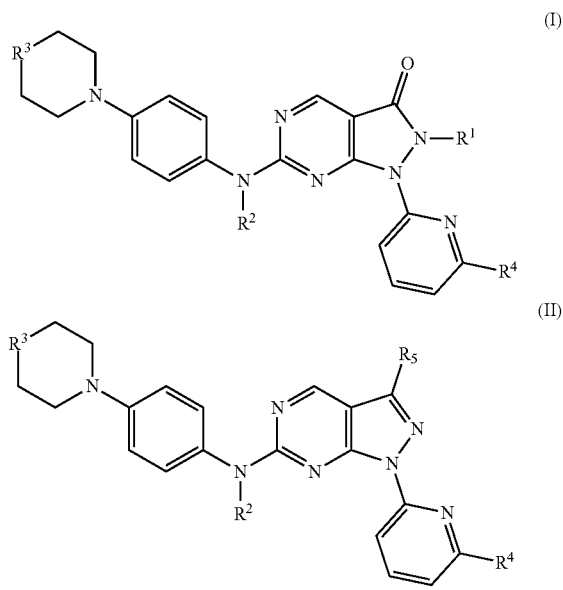

wherein:

R[1] is H, $C_{1-6}$ alkyl, $C_{2-6}$ alkenyl, substituted $C_{1-6}$ alkyl, or substituted $C_{2-6}$ alkenyl;

R[2] is H, aryl, substituted aryl, heteroaryl, substituted heteroaryl, $C_{1-6}$ alkyl, or substituted $C_{1-6}$ alkyl;

R[3] is methylene, oxygen, amine, or nitrogen substituted with $C_{2-6}$ alkyl substituted $C_{1-6}$ alkyl, $C_{1-6}$ alkoxy, or $CO_2R^6$, but where R[3] cannot be N-methyl; and, R[4] is H, or an optionally substituted alkyl ($C_{1-6}$).

R[5] is H, $C_{1-6}$ alkyl, substituted $C_{1-6}$ alkyl, $C_{2-6}$ alkenyl, $C_{1-6}$ alkoxy, aryl, substituted aryl, heteroaryl, substituted heteroaryl, $OR^6$, $SR^6$, $CO_2R^6$, $OC(=O)R^6$, or $NR^7R^8$;

R[6] is H, $C_{1-6}$ alkyl, substituted $C_{1-6}$ alkyl, $C_{3-8}$ cycloalkyl, aryl, substituted aryl, heteroaryl or substituted heteroaryl; and, R[7] and R[8] are independently H, $C_{1-6}$ alkyl, substituted $C_{1-6}$ alkyl, $C_{3-8}$ cycloalkyl, $C_{2-4}$ alkenyl, aryl, substituted aryl, heteroaryl or substituted heteroaryl.

Illustrative compounds of this disclosure include:

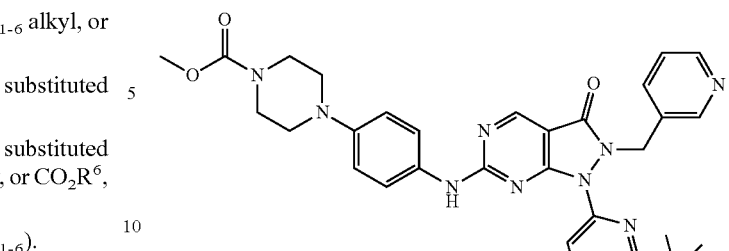

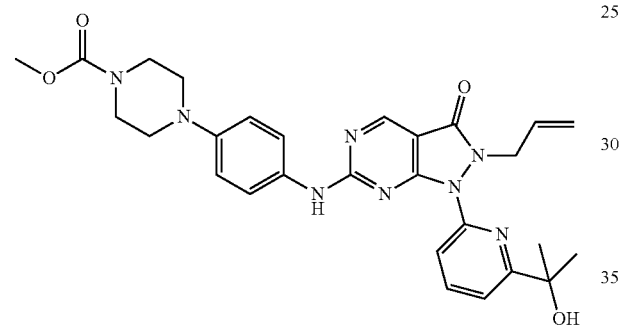

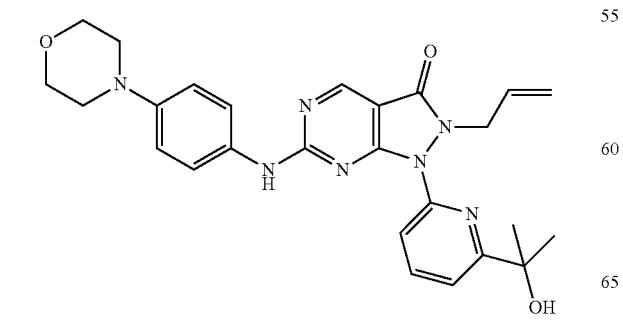

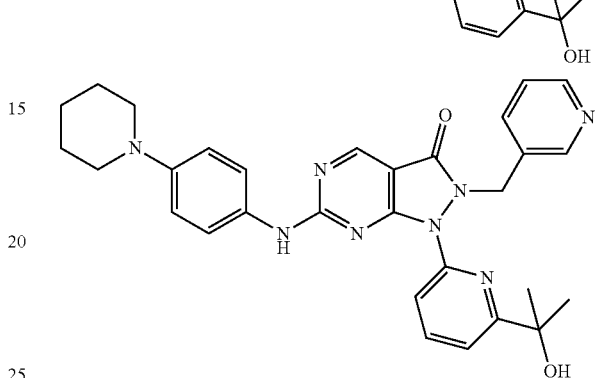

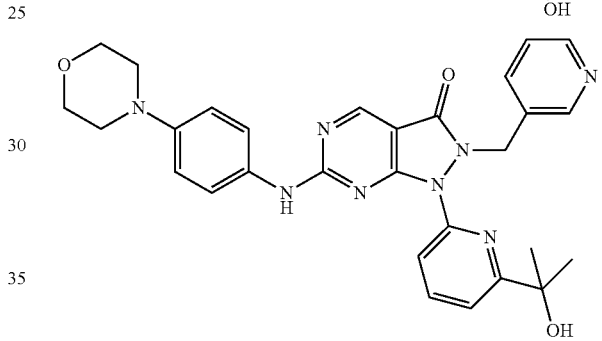

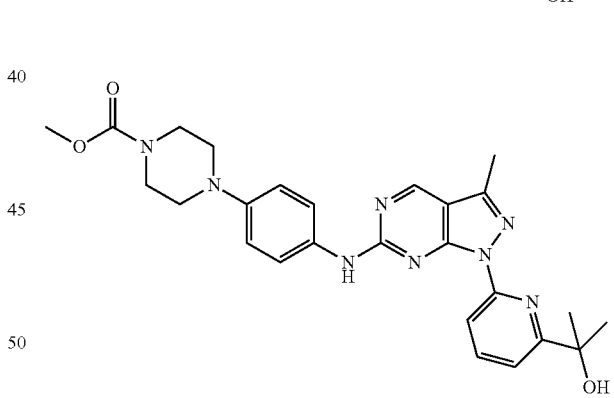

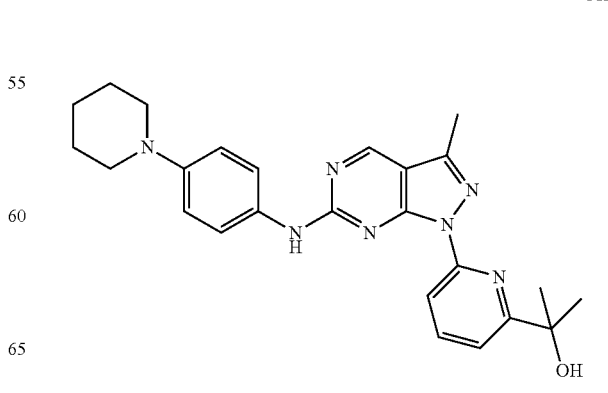

-continued

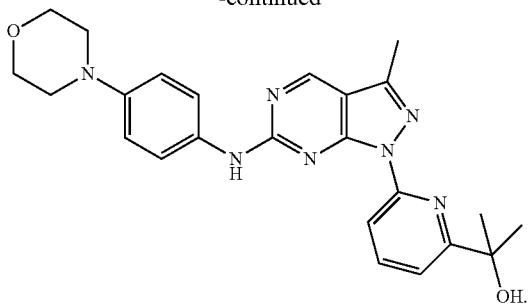

The compounds disclosed herein may be used to prevent, treat, or ameliorate cancer, or prevent metastasis of a cancer in a subject by administering a therapeutically-effective amount of a compound of this disclosure that inhibits Wee1 kinase. For example, the disclosed compounds may be used to treat an advanced solid tumor, a blood cancer, a brain tumor, an ovarian tumor, cervical cancer, squamous cell cancer of the head and neck, pancreatic cancer, and lung cancer. These compounds may be particularly useful in treating the blood cancer acute myeloid leukemia. These compounds are small molecular weight lipophilic compounds with physicochemical properties that readily pass through the blood-brain barrier, thereby successfully treating brain tumors following systemic administration.

Therapeutically effective amounts of the disclosed compounds can be administered to a subject with a tumor to achieve an anti-tumor effect, such as inhibition of tumorigenesis or tumor metastasis. The disclosed compounds are also useful in the treatment of both primary and metastatic solid tumors. The disclosed compounds are also useful in treating hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these compounds may be useful in the treatment of solid tumors arising from hematopoietic malignancies. In addition, these compounds may be useful in the prevention of metastases from the tumors described above either when used alone or in combination with radiotherapy and/or other chemotherapeutic agents. The compounds are also useful in treating multiple myeloma.

Further, a method for inhibiting the activity of the Wee1 kinase in a subject using the disclosed compounds is provided. The method includes administering a therapeutically effective amount of a disclosed compound to a subject to achieve a Wee1 inhibitory effect. The disclosed compounds having Wee1-inhibitory effects are useful for treating many inflammatory, infectious, immunological, and malignant diseases. These include, but are not limited to, cancer, tumor growth, undesirable angiogenesis, and autoimmune diseases.

Wee1 has been implicated in the maintenance and survival of cancer stem cells, including, specifically, glioblastoma (Forte et al PLoS One 2013 8(12):e81432), leukemia (Tuel-Ahlgren et al, Leuk Lymphoma 1996; 20(5-6):417-26; Zhou et al. Leukemia. 2015; 29(4):807-18), breast (Wang et al. Oncologist 2011; 16(7):966-79), and lung (Syljuasen et al. Front Genet. 2015; 6:70) cancers. Thus, further methods for inhibiting the activity of the Wee1 kinase in cancer stem cells using the disclosed compounds is provided. These methods may be particularly effective in preventing metastases of a tumor in a patient and/or treating drug-resistant cancers in a patient, which may include sensitizing cancer cells to other anticancer drugs that may be administered in combination with the Wee1 inhibitors of this disclosure.

The disclosed compounds can be used in combination with other compositions and procedures for the treatment of diseases. For example, a cancer may be treated conventionally with surgery, radiation or chemotherapy in combination with one or more of the Wee1 kinase inhibitor compounds disclosed herein. Additionally, a cancer may be treated conventionally with a chemotherapeutic and one or more of the Wee1 kinase inhibitor compounds disclosed herein may be administered to reduce chemotherapeutic drug resistance of the cancer cells to the conventional chemotherapeutic.

The disclosed compounds exhibiting Wee1-inhibitory activity may be combined with other kinase inhibitory agents. The disclosed compounds exhibiting Wee1-inhibitory activity may be combined with other conventional anticancer therapies, for example, steroids such as dexamethasone and prednisolone.

Examples of other chemotherapeutic agents that can be used in combination with the disclosed compounds include DNA-targeted agents, including DNA alkylating agents and topoisomerase inhibitors, including cisplatin, capecitabine, carboplatin, cyclophosphamide, cytarabine, dauoribicin, docetaxel, doxorubicin, 5-fluorouracil, gemcitabine, methotrexate, paclitaxel, premetrexed, irinotecan temozolomide, topotecan, radiation, or combinations thereof. Particularly useful chemotherapeutic agents that can be used in combination with the disclosed compounds include cisplatin, cytarabine, or temozolomide.

The disclosed compounds also may be combined with radiotherapy employing radioisotopes (such as $^{32}P$, $^{90}Y$, $^{125}I$, $^{131}I$, and $^{177}Lu$), particle beams (such as proton, neutron and electron beams) and electromagnetic radiation (such as gamma rays, x-rays and photodynamic therapy using photosensitizers and visible or ultraviolet rays).

The disclosed compounds may be combined with pharmaceutically acceptable excipients, and optionally sustained-release matrices, such as biodegradable polymers, to form therapeutic compositions. Therefore, also disclosed are pharmaceutical compositions including one or more of any of the compounds disclosed above and a pharmaceutically acceptable carrier. The composition may comprise a unit dosage form of the composition, and may further comprise instructions for administering the composition to a subject to inhibit cancer progression or metastasis, for example, instructions for administering the composition to achieve an anti-tumor effects or to inhibit a pathological cellular proliferation. Such pharmaceutical compositions may be used in methods for treating or preventing cancer growth in a subject by administering to the subject a therapeutically effective amount of the composition.

These pharmaceutical compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Pharmaceutical compositions can be administered systemically or locally in any manner appropriate to the treatment of a given condition, including orally, parenterally, intrathecally, rectally, nasally, buccally, vaginally, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions may readily penetrate the blood-brain barrier when peripherally or intraventricularly administered.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. Oral liquid preparations can be in the form of, for example, aqueous or oily suspensions, solutions, emulsions, syrups or elixirs, or can be presented as a dry product for reconstitution with water or other suitable vehicle before use.

The pharmaceutical compositions can also be administered parenterally in a sterile aqueous or oleaginous medium. The composition can be dissolved or suspended in a non-toxic parenterally-acceptable diluent or solvent, e.g., as a solution in 1,3-butanediol. Commonly used vehicles and solvents include water, physiological saline, Hank's solution, Ringer's solution, and sterile, fixed oils, including synthetic mono- or di-glycerides, etc. For topical application, the drug may be made up into a solution, suspension, cream, lotion, or ointment in a suitable aqueous or non-aqueous vehicle. Additives may also be included, for example, buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentration that has been shown to be active in vitro, in vivo, or in tissue culture. For example, a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day can be useful for treatment of a particular condition.

The compounds can be used in the form of pharmaceutically acceptable salts derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.). Basic nitrogen-containing groups can be quaternized, for example, with such agents as $C_{1-8}$ alkyl halides (such as methyl, ethyl, propyl, and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

Each publication or patent cited herein is incorporated herein by reference in its entirety. The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1 the Identification of Wee1 Kinase in Brain Cancer

To identify novel molecular targets for medulloblastoma therapy, the inventors performed an integrated genomic screen using pathway analysis of gene expression in tumor tissue and a kinome-wide siRNA screen in the Daoy medulloblastoma cell line. The inventors performed gene expression profiling on 16 medulloblastoma and 3 normal cerebellar tissue samples, measured by Affymetrix microarrays (Int J Cancer. 2012; 131(8):1800-9). A pathway analysis was performed using IPAsoftware (Ingenuity) and gene set enrichment analysis to identify specific signaling networks. Cell cycle-related genes were the most abundant in the molecular category and kinases were the most abundant in the functional category. The comparison of the molecular and functional categories with the total dysregulated genes in medulloblastoma identified 50 specific genes (FIG. 1A), with 29 significantly overexpressed in medulloblastoma compared with normal cerebellum. The inventors then performed a kinome-wide siRNA screen to identify kinases that are essential for medulloblastoma cell proliferation. The medulloblastoma Daoy cell line was transfected with 2130 siRNAs targeting each of 710 kinase genes or a non-silencing control.

Figure 1B:
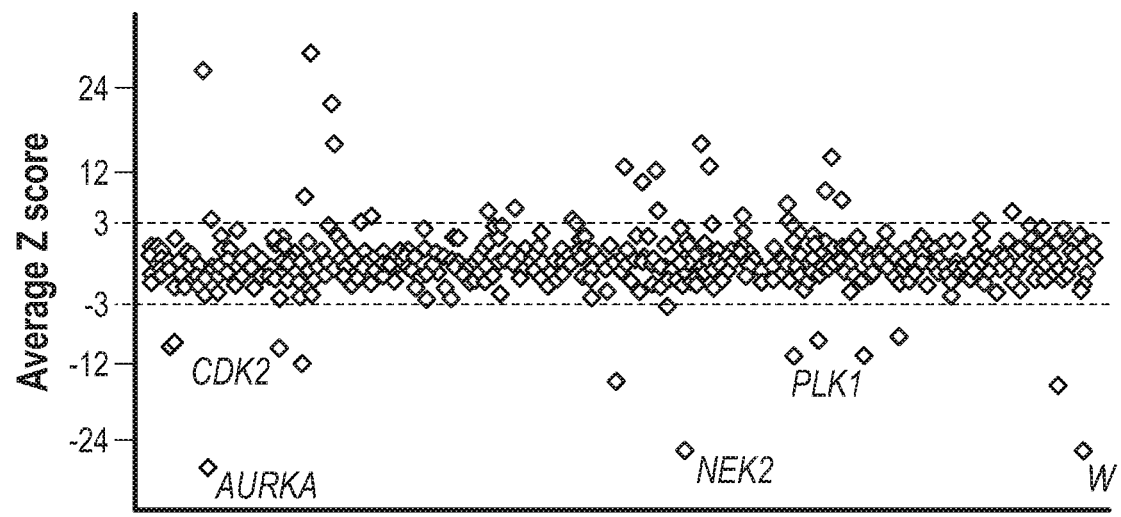
Figure 1C:
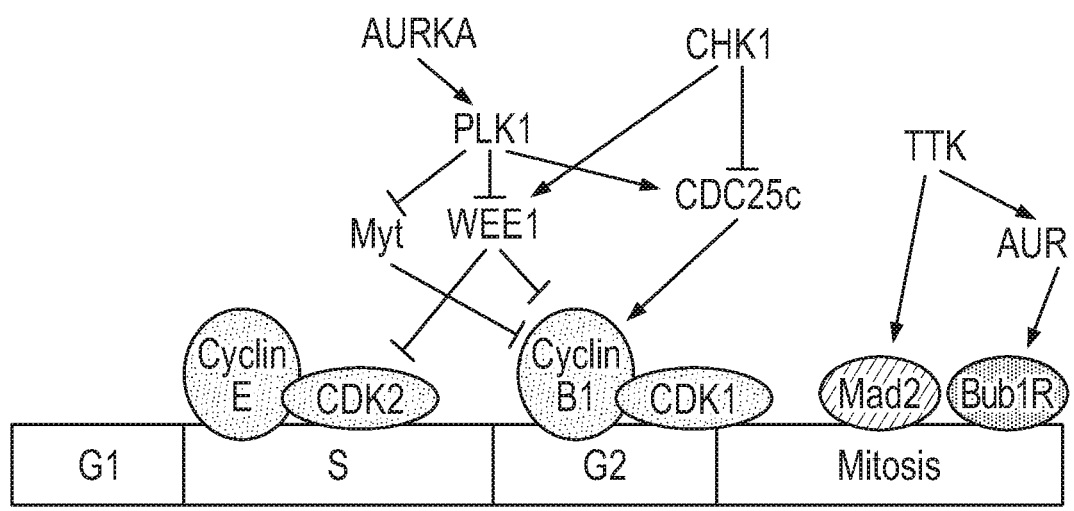

Cell proliferation was evaluated by MTS assay after 72 hours of transfection. Absorbance values were normalized to controls and the average Z score was calculated. A total of 95 genes were identified (Z score of <2) that decreased Daoy cell growth when inhibited (FIG. 1B). The combined analysis of the 29 genes overexpressed from the gene expression data and the 95 kinases identified in the siRNA screen identified cell cycle-related kinases in the G2 checkpoint, implicating the G2 checkpoint control as a target for medulloblastoma therapy (FIG. 1C).

Many cancers possess a deficient G1 checkpoint that impairs the ability of the cell to halt the cell cycle to repair DNA damage prior to replication (Drug Discovery Today. 2012; 17(5-6):194-202). This gives cancer cells a means to accumulate mutations and propagate irregularities that are favorable to cancer formation. In normal cells, the G1 checkpoint is not compromised; therefore, the G2 checkpoint is not burdened with halting the cell cycle prior to DNA damage repair. This supports that abrogation of the G2 checkpoint will selectively impact tumorigenesis rather than normal cell growth. The inventors' combined genomic analysis and siRNA screen identified Wee1 as a focal kinase in two signaling pathways (FIG. 1C) demonstrating that targeting Wee1 for inhibition has the potential to disrupt multiple tumor survival mechanisms.

Wee1 is a tyrosine kinase that is a critical component of the ATR-mediated G2 cell cycle checkpoint control that prevents entry into mitosis in response to cellular DNA damage (Cell Cycle. 2 013; 12(19):3159-64). ATR phosphorylates and activates CHK1, which in turn activates Wee1, leading to the selective phosphorylation of cyclin-dependent kinase 1 (CDK1) at Tyr5, thereby stabilizing the CDK1-cyclin B complex and halting cell-cycle progression. This process confers a survival advantage by allowing tumor cells time to repair damaged DNA prior to entering mitosis. Inhibition of Wee1 abrogates the G2 checkpoint, forcing cancer cells with DNA damage to enter into unscheduled mitosis and undergo cell death via mitotic catastrophe.

Example 2 the Role of Wee1 in Cancer

Figure 2A:
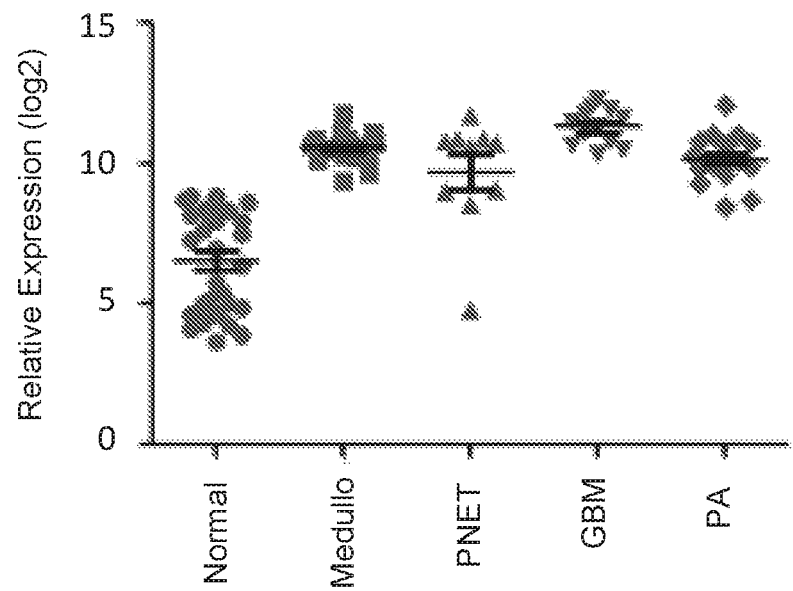
FIGS. 2A-2C show Wee1 expression in medulloblastoma.

The inventors have examined the expression of Wee1 in a panel of pediatric brain tumors and found Wee1 to be overexpressed in the high-grade tumors including medulloblastoma (medullo), primitive neuroectodermal tumor (PNET) and pediatric GBM, and in the low-grade pilocytic astrocytoma (PA) compared with normal brain (FIG. 2A). These data support increased Wee1 expression is implicated in tumorigenesis.

Figure 2B:
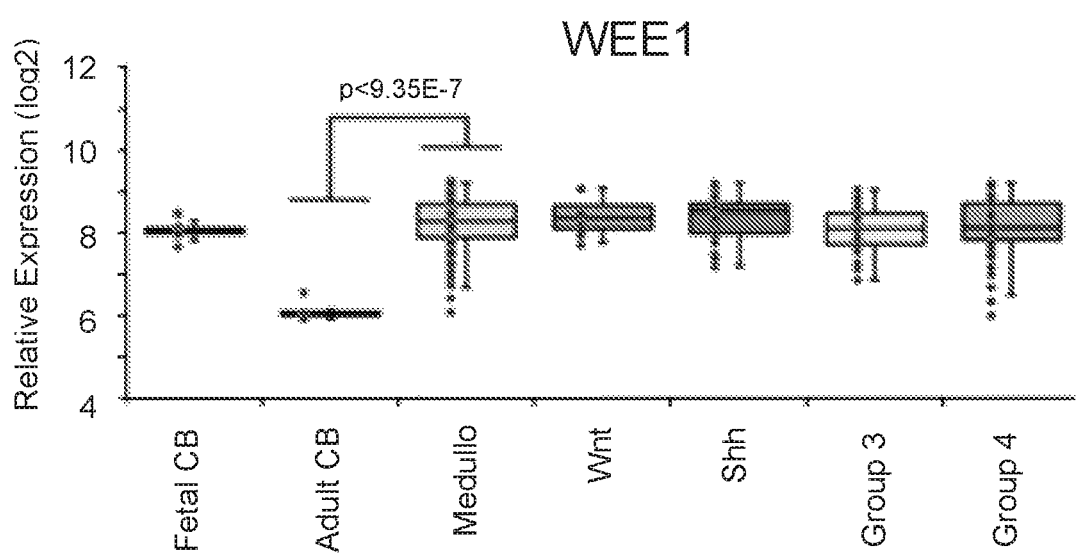
Figure 2C:
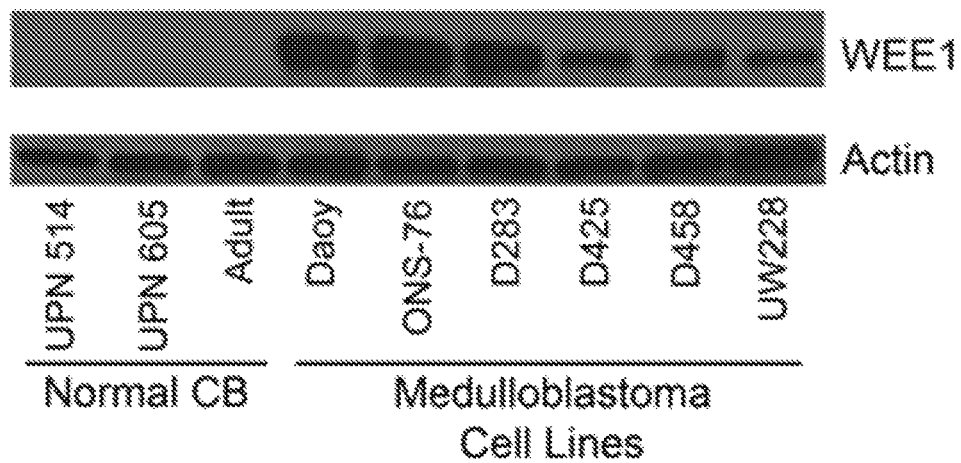
Figure 3A:
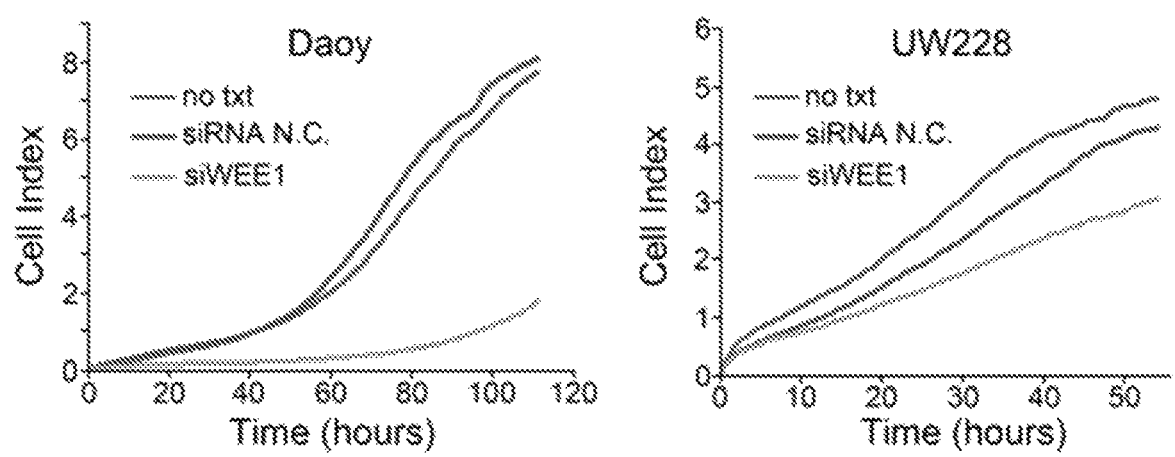
FIGS. 3A and 3B show siRNA-mediated Wee1 inhibition decreases medulloblastoma cell proliferation.
Figure 3B:
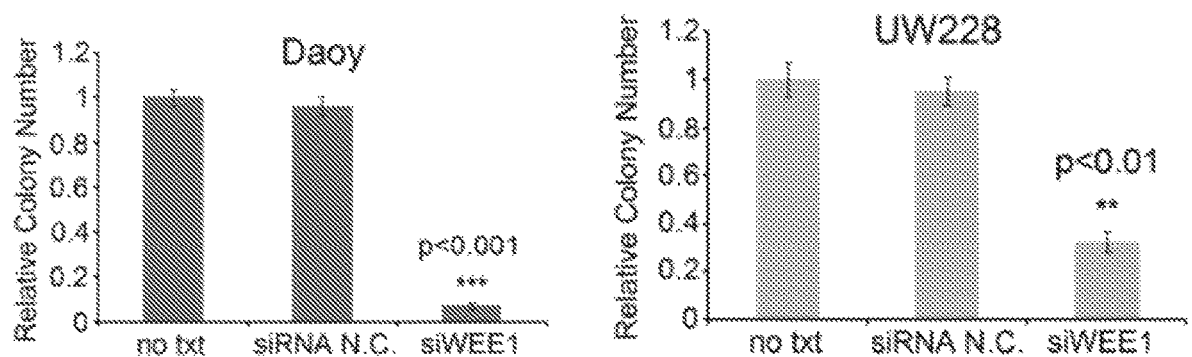

To further support targeting Wee1 in medulloblastoma the inventors examined the expression of Wee1 in 90 medulloblastoma tissue samples (FIG. 2B). There was significant overexpression of Wee1 in the medulloblastoma tissue compared with normal cerebellum, and importantly there was no significant difference in Wee1 expression between the 4 medulloblastoma sub-groups (Wnt, Shh, Group 3 and Group 4), suggesting that targeting medulloblastoma would be effective in all sub-groups. Furthermore, the inventors evaluated Wee1 expression in a panel of well-characterized medulloblastoma cell lines (FIG. 2C). Wee1 was not present in pediatric (UPN 514 and 605) or adult cerebellum tissue samples, but was present in the 6 medulloblastoma cell lines. To determine the functional consequence of inhibiting Wee1 the inventors used siRNA against Wee1 and measured cell proliferation using the xCELLigence real-time cell analysis (RTCA) system in Daoy and UW228 cells. A decrease in cell growth was observed in the Daoy and UW228 cell lines (FIG. 3A). Then the inventors used the colony-forming assay to determine the ability of medulloblastoma cells to undergo an unlimited number of divisions following inhibition of Wee1 by siRNA. The siRNA targeting Wee1 showed a decrease in the relative colony number compared with the non-silencing siRNA in Daoy and UW228 cell lines (FIG. 3B).

Several small molecule inhibitors of Wee1 have been described (Clin Cancer Res. 2011; 17(13):4200-7; Mol Cancer Ther. 2009; 8(11):2992-3000; Cancer Cell. 2010; 18(3):244-57), but none are highly selective for Wee1 and the most potent, AZD1775, is currently being evaluated in clinical trials in combination with DNA damaging agents for several cancer types. A high-throughput screen (HTS) conducted by Merck Research Laboratories on a small chemical compound library identified MK1775 (now known as AZD1775) as a small-molecule nanomolar inhibitor of Wee1 kinase. Inhibition of Wee1 by AZD1775 has been shown in some cancers to abrogate the G2 checkpoint, forcing cancer cells with DNA damage to enter unscheduled mitosis to undergo cell death (Cancer biology & therapy. 2010; 9(7):523-5; Current clinical pharmacology. 2010; 5(3):186-91). Like Chk1, inhibition of Wee1 in combination with DNA-damaging agents has been explored as a therapeutic strategy for tumors with dysregulated p53 (Clinical cancer research, 2011; 17(17):5638-48). However, Wee1 is downstream of Chk1; therefore, inhibition of Wee1 kinase activity is less likely to produce the severe side effects associated with the inhibition of the upstream master regulators. The inventors have shown that Wee1 inhibition by the small molecule inhibitor AZD1775 suppressed cell growth, induced apoptosis, and decreased tumor growth as a single agent and displayed synergistic activity with cisplatin in medulloblastoma cells (Mol Cancer. 2014; 13:72). Furthermore, the inventors' data suggests that cell growth inhibition induced by AZD1775 as a single agent is independent of p53 status in medulloblastoma and acute myelogenous leukemia (AML) cell lines (Mol Cancer Ther. 2013; 12(12):2675-84). Collectively, their data support that Wee1 is a promising candidate for targeted therapy in medulloblastoma and that inhibition of Wee1 kinase activity has the potential to chemosensitize the tumor to DNA-damaging agents.

The structure-activity relationship (SAR) data for AZD1775 is limited, as it was not developed through a focused medicinal chemistry effort, but discovered from a HTS, and it is known to have nanomolar activity with at least 8 other kinases. This lack of SAR and kinase selectivity data and the potent single agent cellular toxicity of AZD1775 was a concern as off-target effects resulting in cellular toxicity that are unrelated to Wee1 inhibition may exacerbate therapy-related adverse effects in patients with medulloblastoma. Although AZD1775 has been reported to be "well-tolerated" in clinical trial, there has been no single agent safety and tolerability study for AZD1775 and its toxicity could be masked by combination therapies. These concerns supported the inventors' development of new selective Wee1 inhibitors for the treatment of medulloblastoma. The inventors developed a small series of Wee1 inhibitors based on AZD1775 to establish assay systems and further examine the effects of Wee1 inhibition in medulloblastoma. Interestingly, the inventors' compounds that inhibited Wee1 in the same nanomolar range as AZD1775 in an in vitro kinase assay, did not exhibit the same potent inhibitory effect on medulloblastoma cell growth as single agents, yet these compounds reduced pCDK levels and demonstrated synergy with cisplatin at non-toxic inhibitor concentrations. The inventors now develop inhibitors with improved selectivity for Wee1, evaluating their single agent cytotoxicity, synergy with cisplatin, blood-brain barrier (BBB) penetration, pharmacokinetic profiles, and inhibition of tumor growth in xenograft models.

Example 3: Developing Selective Small Molecule Inhibitors of Wee1 Kinase

Figure 6A:
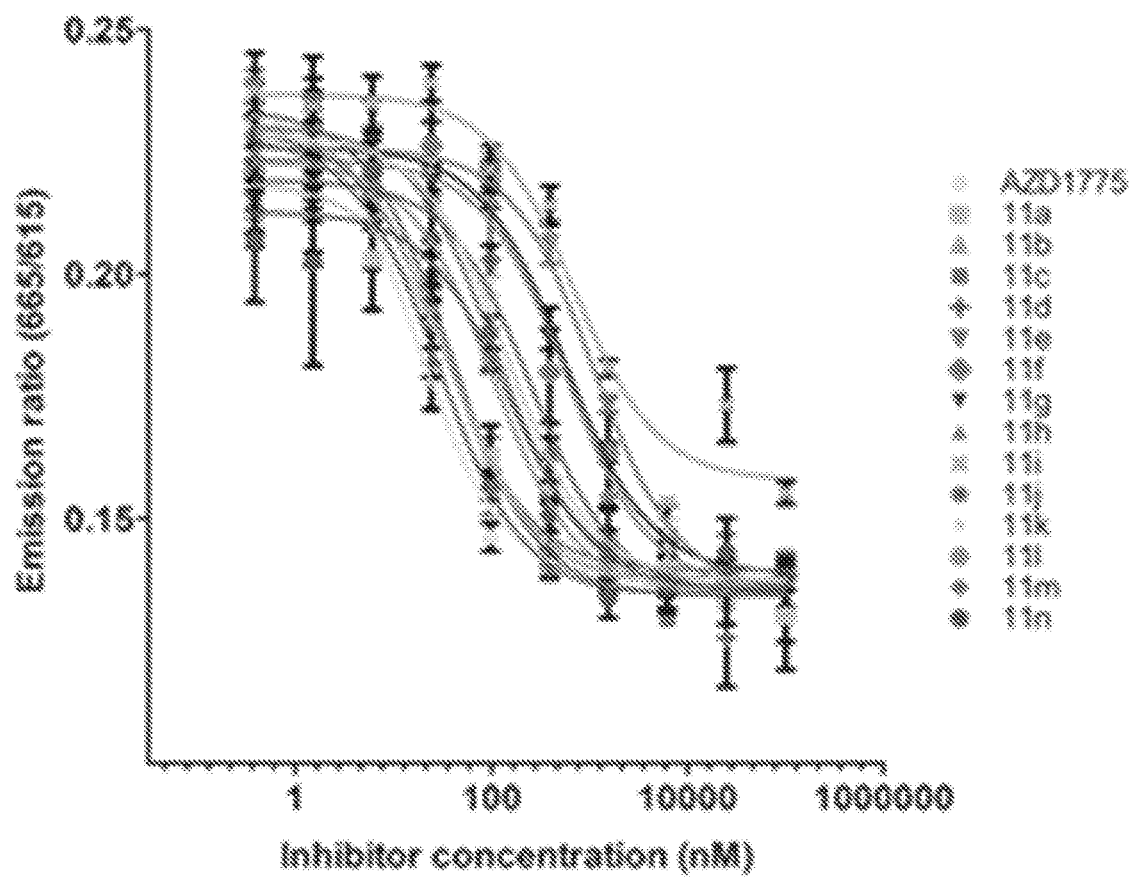
FIGS. 6A and 6B show a dose-response of Wee1 inhibition by AZD1775 analogs from an in vitro kinase activity assay.
Figure 4:
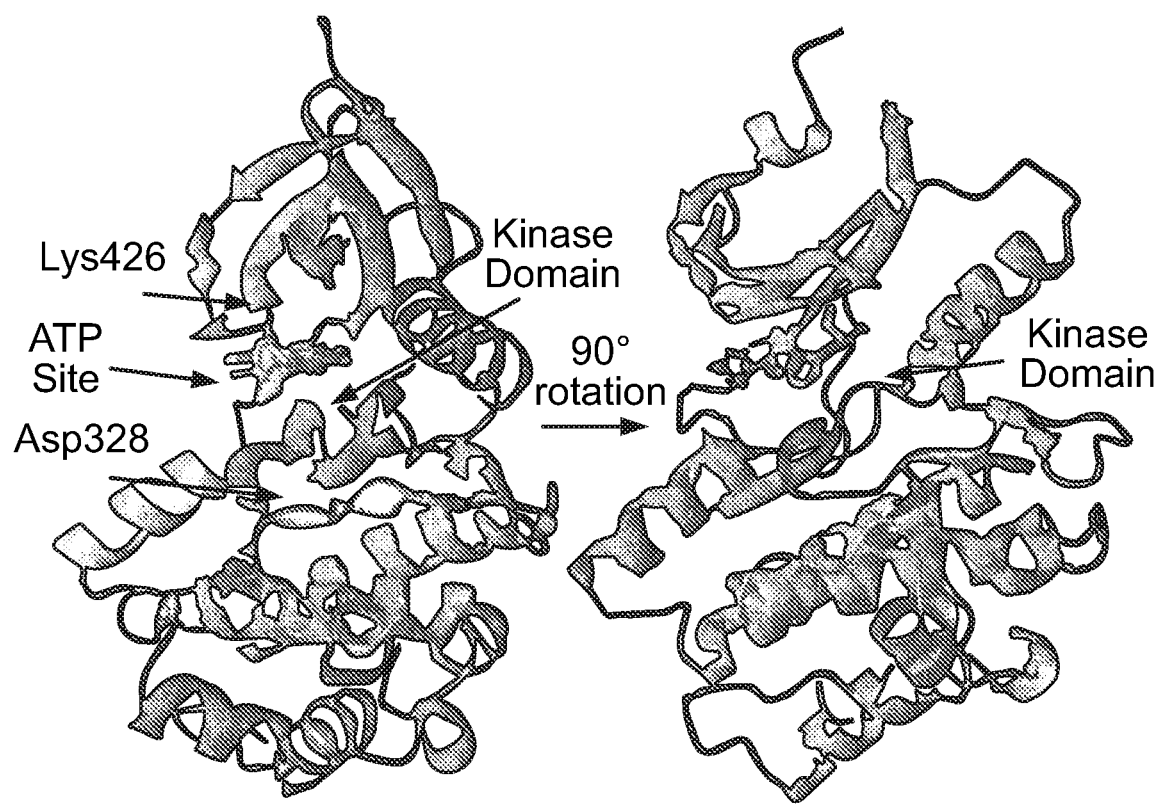
FIG. 4 depicts AZD1775 docked into the ATP-binding domain of Wee1. Ribbon representation of Wee1 showing the ATP-binding site (Lys426 site reference), kinase domain (Asp328 site reference), and docked MK1775 (carbons colored orange).
Figure 5A:
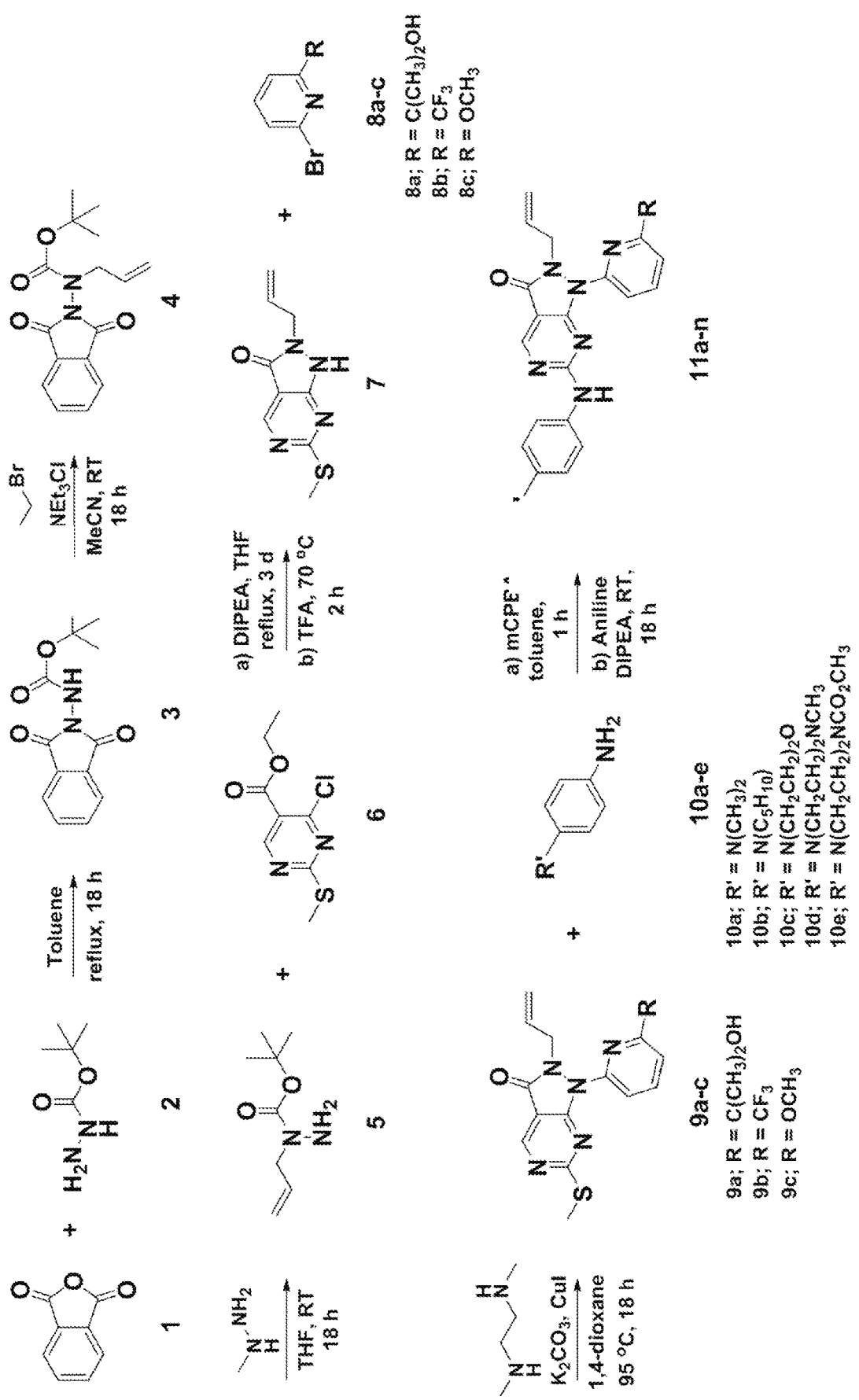
Figure 6B:
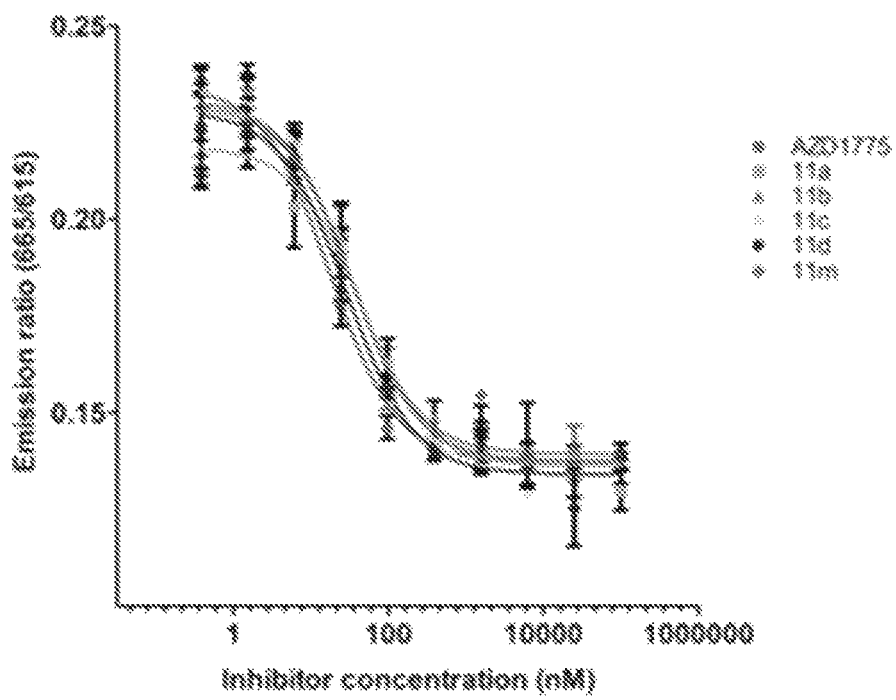

Computational-based molecular docking of AZD1775 into the ATP-binding site of Wee1 using the Glide docking protocol within Maestro (Schrödinger) revealed the interactions between AZD1775 and Wee1 and indicated that the 4-methylpiperazinyl and pyridyl-2-propan-2-ol side chains were orientated towards the entrance of the binding cavity, where a range of potential substitutions could be accommodated (FIG. 4). From the model, the 4-methylpiperazinyl group can interact with Ile305, Tyr378 and Cys379 via hydrophobic and π-alkyl interactions. To understand the extent of these interactions, a series of compounds were proposed that retain the dialkylanilino group, whilst sequentially building complexity in this region with dimethylamino, piperadine, morpholine and piperazine N-methyl ester groups. The pyridyl-2-propan-2-ol substituent in AZD1775 was predicted to make an edge-face π-π interaction with Phe433. To confirm the amenability of this group to modification, 2-trifluoromethlpyridine and 2-methoxypyridine were identified that would retain this π-π interaction, whilst being structurally diverse from the propan-2-ol group in AZD1775. All possible combinations of the compounds (11a-n) and AZD1775 were synthesized (FIG. 5), and the IC50 values were determined in an in vitro recombinant Wee1 kinase activity assay (FIGS. 5 and 6). All the compounds retaining the pyridyl-2-propan-2-ol substituent (11a-d) of AZD1775 demonstrated potent Wee1 inhibition. However, when the pyridine ring was modified only compound 11 m, with the 2-methoxy pyridinyl substitution and retaining the 4-methylpiperazinyl group, demonstrated inhibition comparable with AZD1775. These data indicate that, although AZD1775 is amenable to modification, small structural changes in the side chains can impact Wee1 inhibitory activity.

Figure 7A:
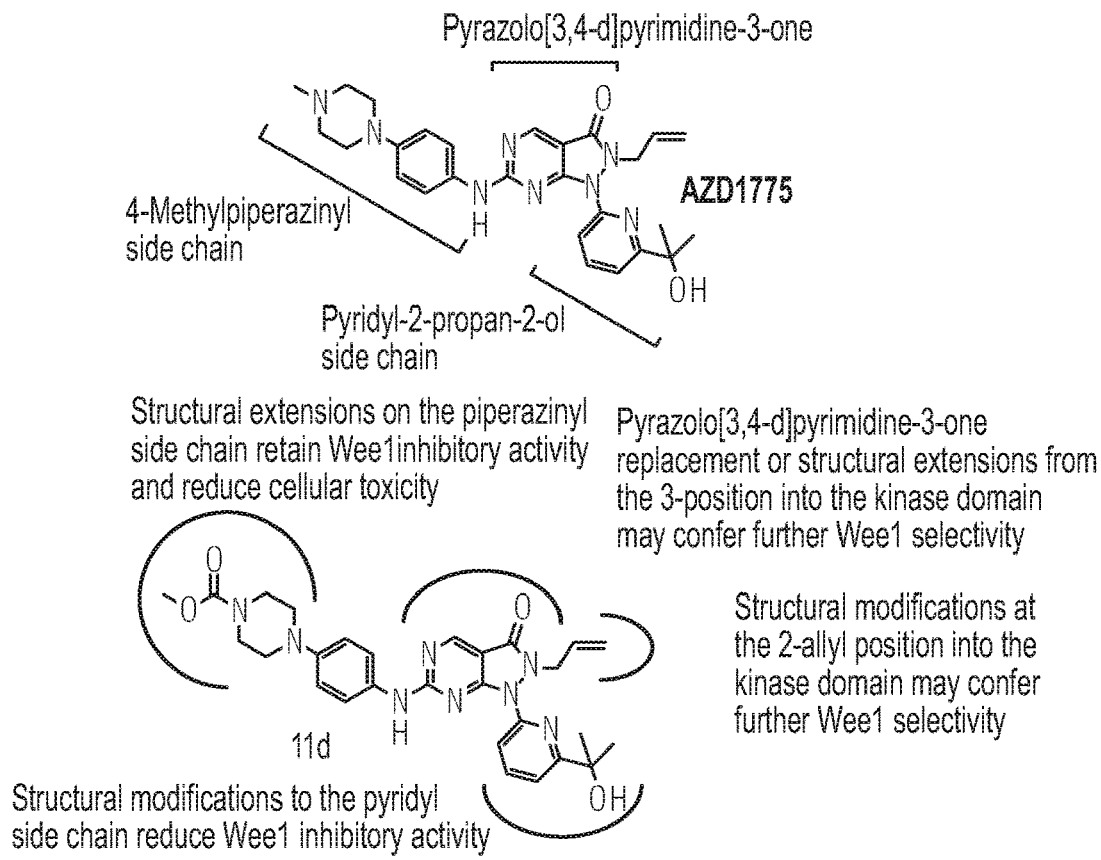
FIGS. 7A and 7B show the structure of AZD1775 and 11d and predicted BBB penetration.
Figure 7B:
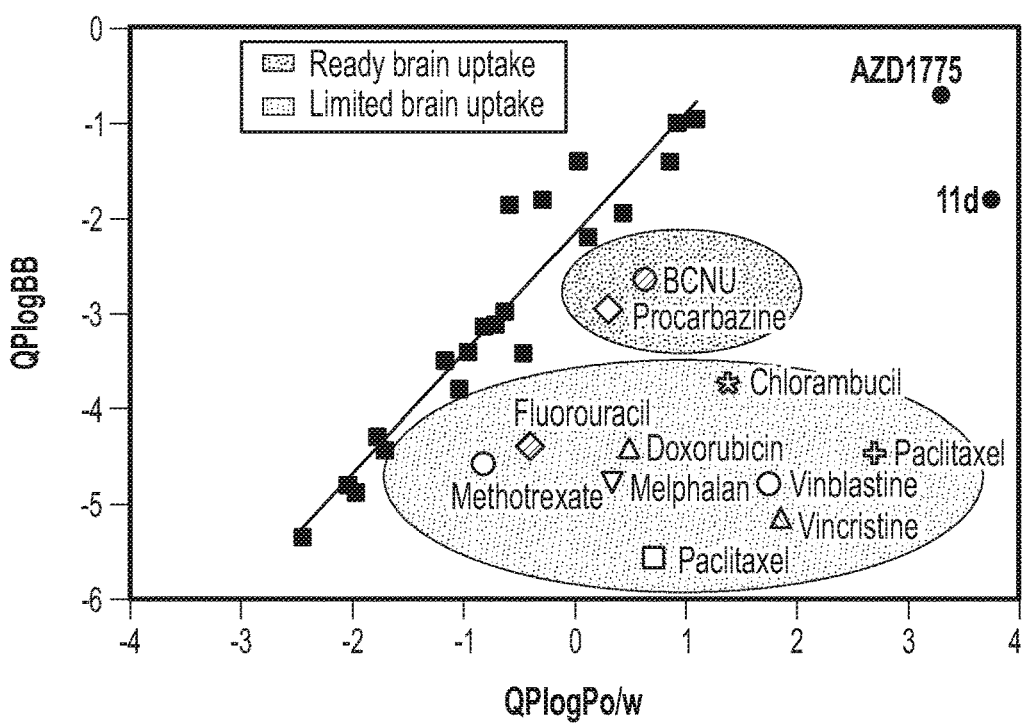

The analogs of AZD1775 which the inventors have synthesized (FIG. 5) were designed by modifying two of the side chain substitutents around the core pyrazolo[3,4-d]pyrimidin-3(2H)-one structure. These 14 AZD1775 analogs have provided useful structural data and the inventors have identified which substituents maintain inhibitory activity. The inventors have also performed an examination of substitutions at the 2-position of pyrazolo[3,4-d]pyrimidin-3(2H)-one ring, replacing the allyl group, and it appears that alkyl 5-6 membered nitrogen-containing heterocyclics are preferred. Compounds are also examined based on their predicted BBB penetration. For the blood-brain partition coefficient (qplogBB) calculated in Quikprop a range of −3.0 to 1.2 is recommended for good BBB penetration; however, the limits for experimentally derived BBB penetration ranges between −2.0 and 1.0. As a result, more stringent rules have been applied to calculated log BB values where >0.3 is excellent and >−1.0 is considered poor, for improved correlation with experimental values. A qplogBB of −0.89 was calculated for AZD1775 and −1.8 indicating little ability to cross the BBB; therefore, there is clear scope to improve the BBB penetration of AZD1775 and 11d (FIG. 7B).

Figure 8A:
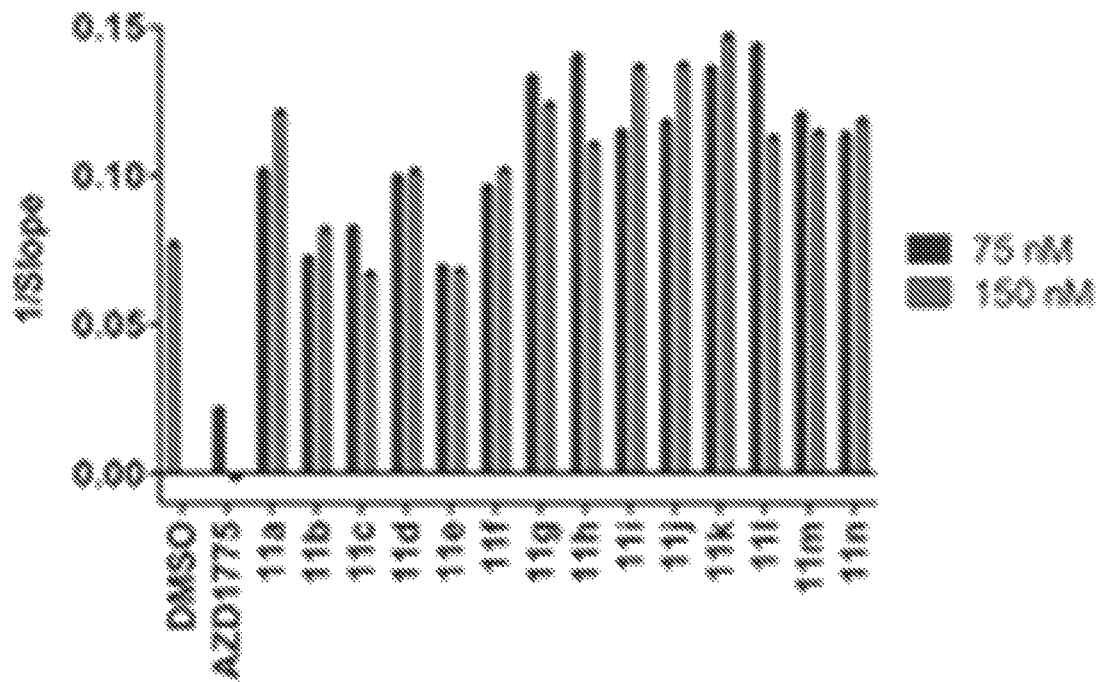
FIGS. 8A-8D show the single agent toxicity of AZD1775 is significantly higher than the AZD1775 analogs.
Figure 8B:
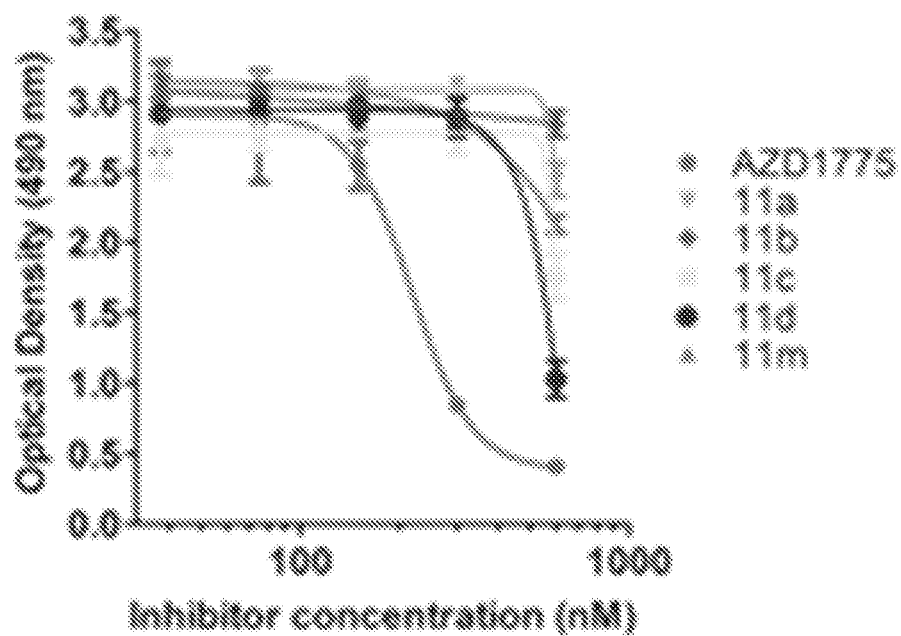
Figure 8C:
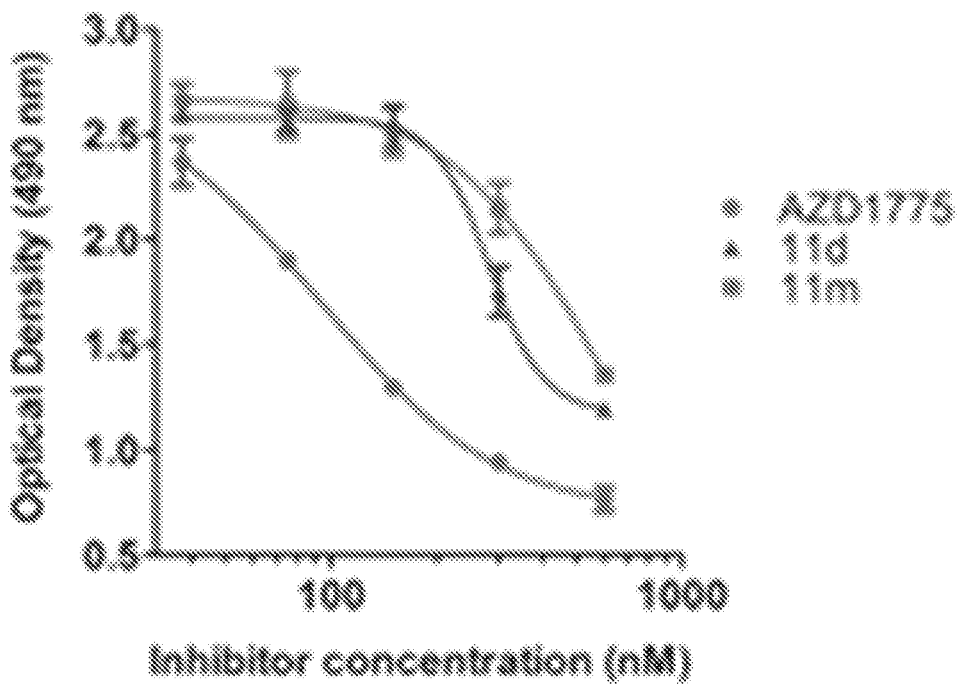
Figure 8D:
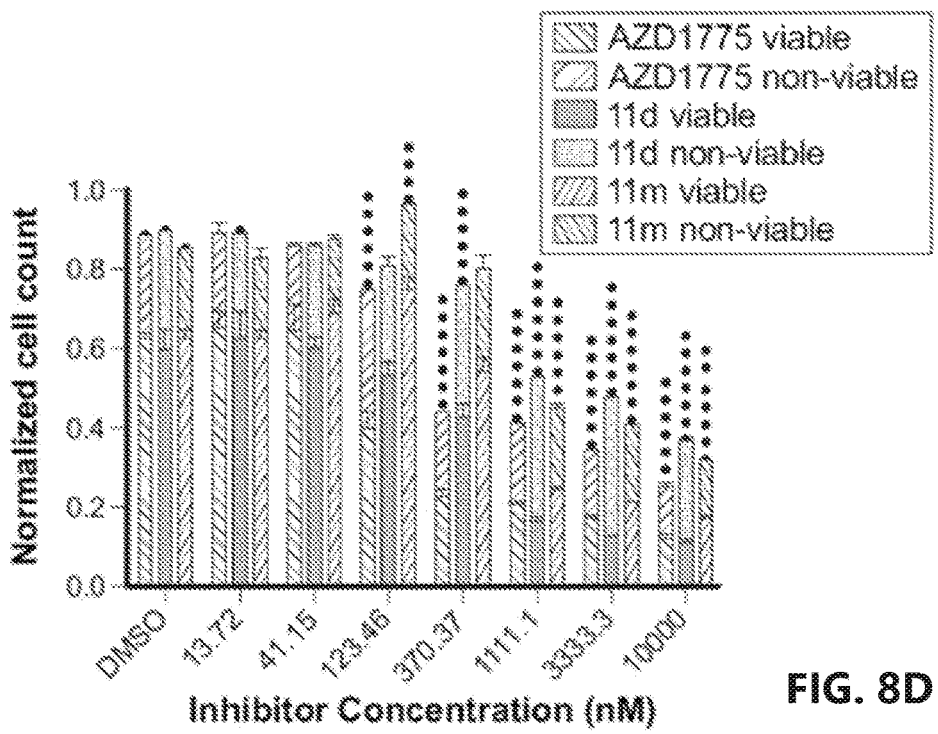

Example 4 Examining the Effect of Wee1 Inhibitors on Cellular pCDK, their Kinase Selectivity and Toxicity as Single Agents, and Synergy with Cisplatin The inventors have previously shown that AZD1775 has a significant impact on the reduction in the growth and viability of medulloblastoma cells as a single agent. In order to evaluate the effect of the AZD1775 analogs, Daoy cells were treated with AZD1775 and compounds 11a-11n, at 75 nM and 150 nM, and cell growth was monitored in real-time using xCELLigence analysis (FIG. 8A). Surprisingly, all compounds 11a-11n, including those with similar inhibitory activities as AZD1775 in the in vitro kinase assay (11a-d, 11m), had minimal impact on cell growth compared with AZD1775. In contrast, AZD1775 resulted in a significant reduction in cell growth at 75 nM, and a net loss in cell number at 150 nM. This difference in single agent cellular effect was further observed between AZD1775 and the Wee1 inhibitors of this disclosure (11a-d, 11m) by MTS assay (FIGS. 8B and 8C). Although AZD1775 had a significant effect on cell viability (Daoy; EC50=219±26 nM, ONS-76; EC50=289±47 nM), these Wee1 inhibitors had little effect within the assay concentration range against Daoy cells, and our most potent Wee1 inhibitors 11d and 11m exhibited a no effect against ONS-76 cells, preventing EC50 determination. The inventors further compared AZD1775 with 11d and 11m over a concentration range in the medulloblastoma D458 suspension cell line, using flow cytometry to determine cell number and percentage viability. Cell number decreased and the percentage of non-viable cells increased compared with DMSO control at a lower concentration of AZD1775 (123.5 nM, p<0.01) than 11d (370.4 nM, p<0.01) and 11m (1.11 µM, p<0.001) (FIG. 8D). These results for AZD1775 as a single agent are concerning as the cells have not been exposed to a DNA damaging agent and without DNA damage there is no requirement for Wee1 to halt the cycle. In addition, the Wee1 inhibitors of this disclosure (11a-d and 11m) demonstrated the same nanomolar activity as AZD1775 in the in vitro kinase activity but had a minimal effect on cell growth inhibition. These data suggest that the effects of Wee1 inhibition may be uncoupled from the potent growth inhibitory activity exhibited by AZD1775. These data suggest that even small changes in the inhibitor structure that maintain Wee1 inhibitory activity in the in vitro kinase assay may not result in potent inhibition of cell growth. A desired characteristic of a chemosensitizing agent is minimal toxicity to confer selective sensitization to the tumor cells and to reduce the impact of adverse effects associated with DNA damaging agents.

Figure 9A:
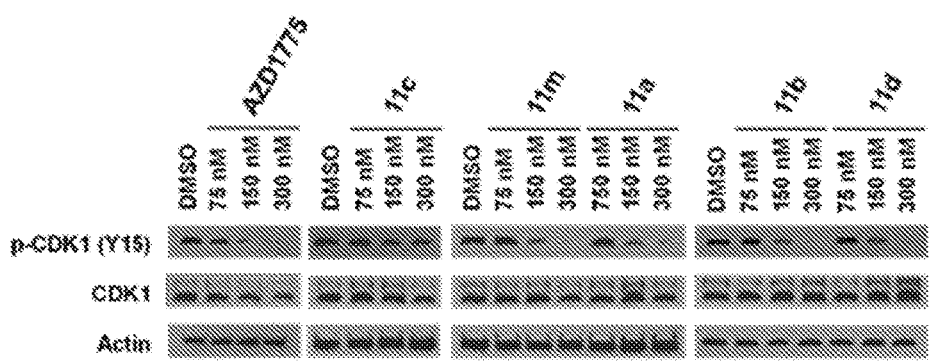
FIGS. 9A and 9B show AZD1775 decreased cellular CDK1 phosphorylation at Tyr5 at lower concentrations than potent novel Wee1 inhibitors.
Figure 9B:
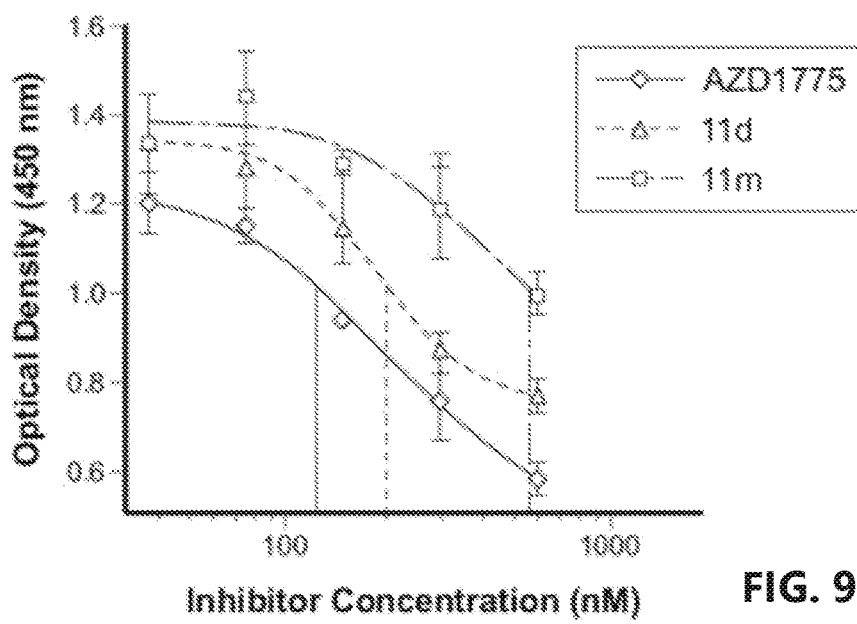
Figure 10A:
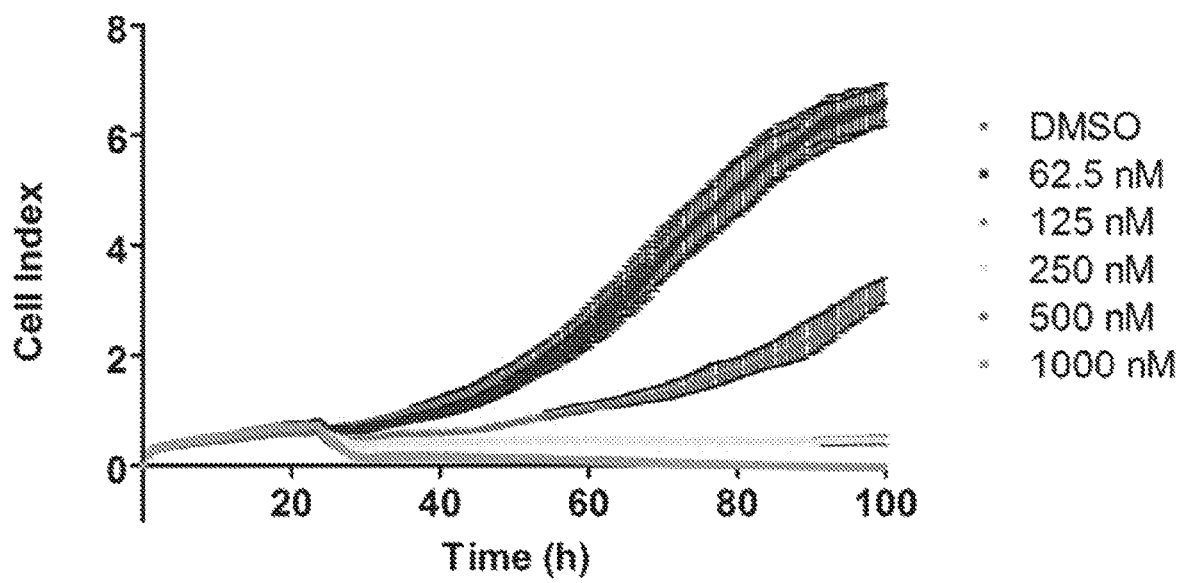
FIGS. 10A-10D show that AZD1775 has an increased inhibitory effect on cell growth compared with 11d at a concentration known to result in comparable cellular Wee1 inhibition. Real-time cell proliferation plots (xCELLigence) for Daoy cells exposed to AZD1775 (FIG. 10A), 11d (FIG. 10B) and 11m (FIG. 10C), recorded for 76 hours post-treatment (drug added at 24 hours).
Figure 10B:
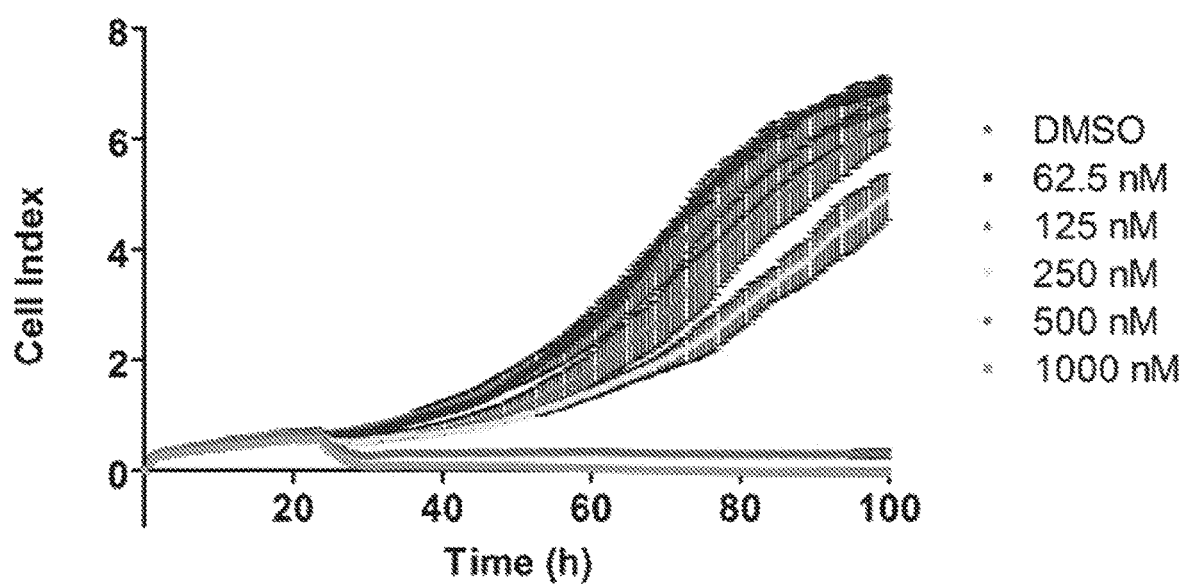
Figure 10C:
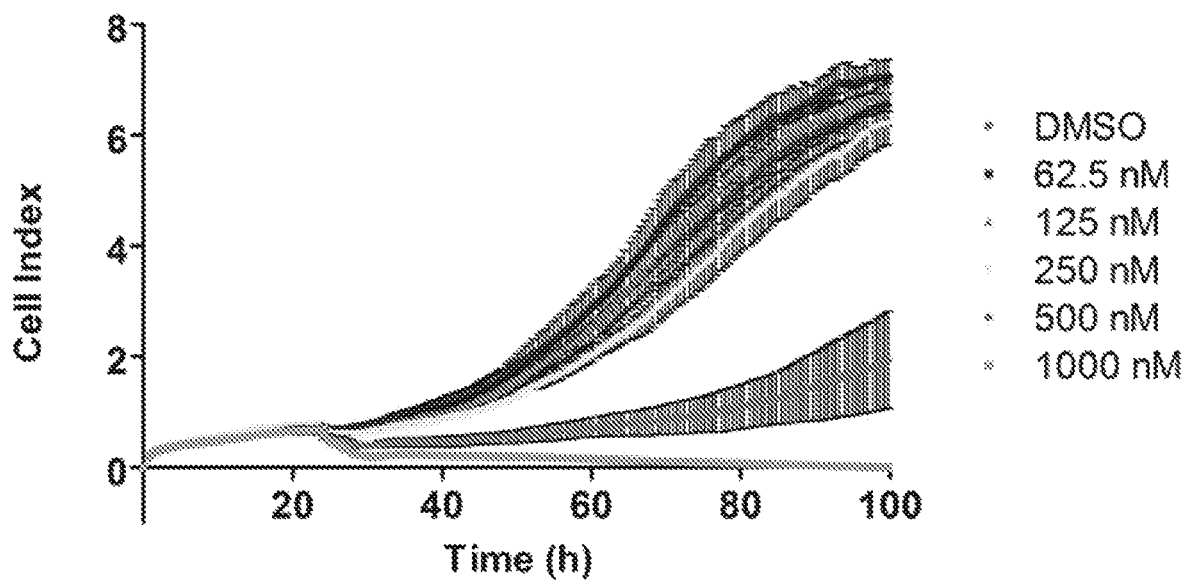
Figure 10D:
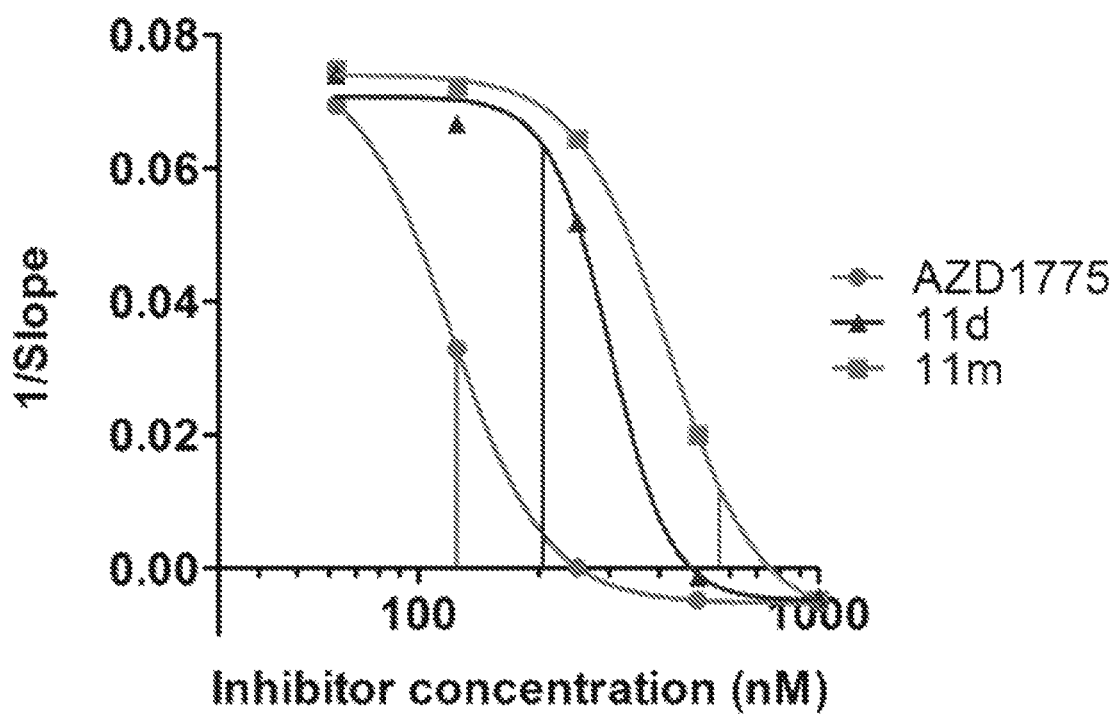
Figure 11A:
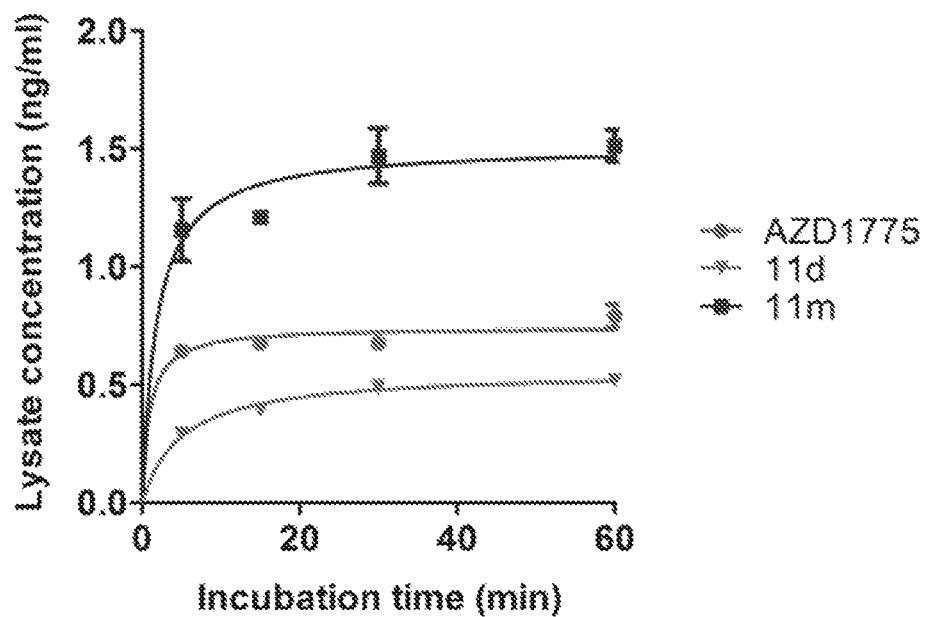
FIGS. 11A-11E show the cell permeability and retention of AZD1775 and novel Wee1 inhibitors. Inhibitor concentration, as determined by LC-MS/MS, in Daoy cell lysate following incubation with AZD1775 (red), 11d (green) and 11m (blue) for 5, 15, 30 and 60 minutes prior to media aspiration and washing.
Figure 11B:
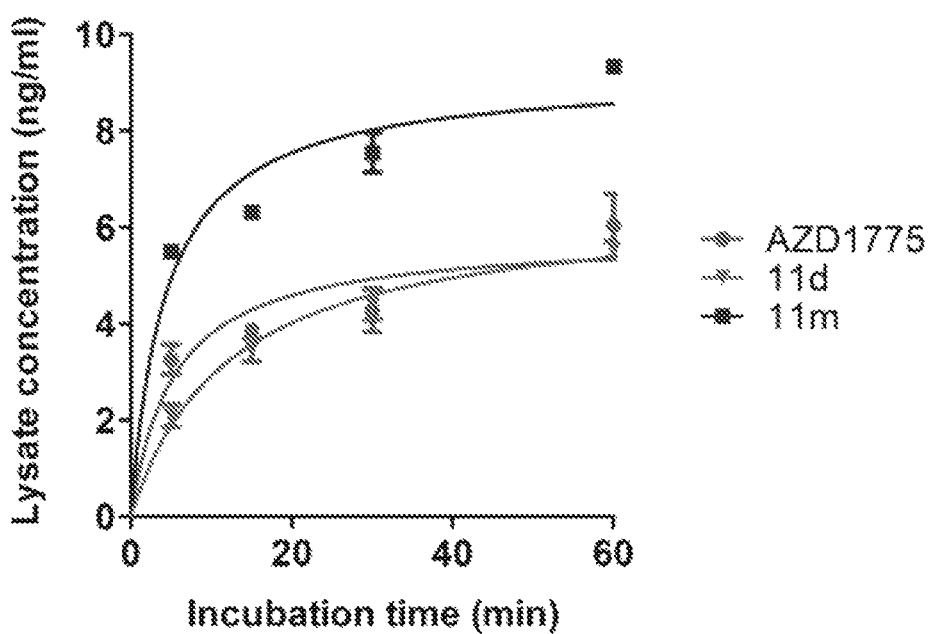
Figure 11C:
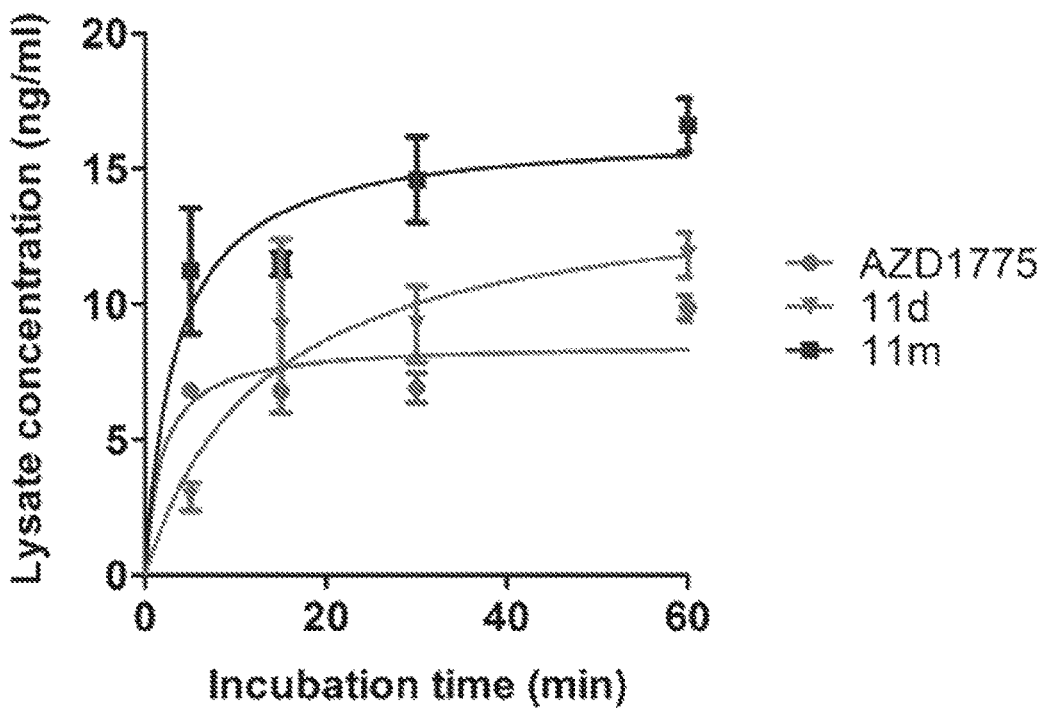
Figure 11D:
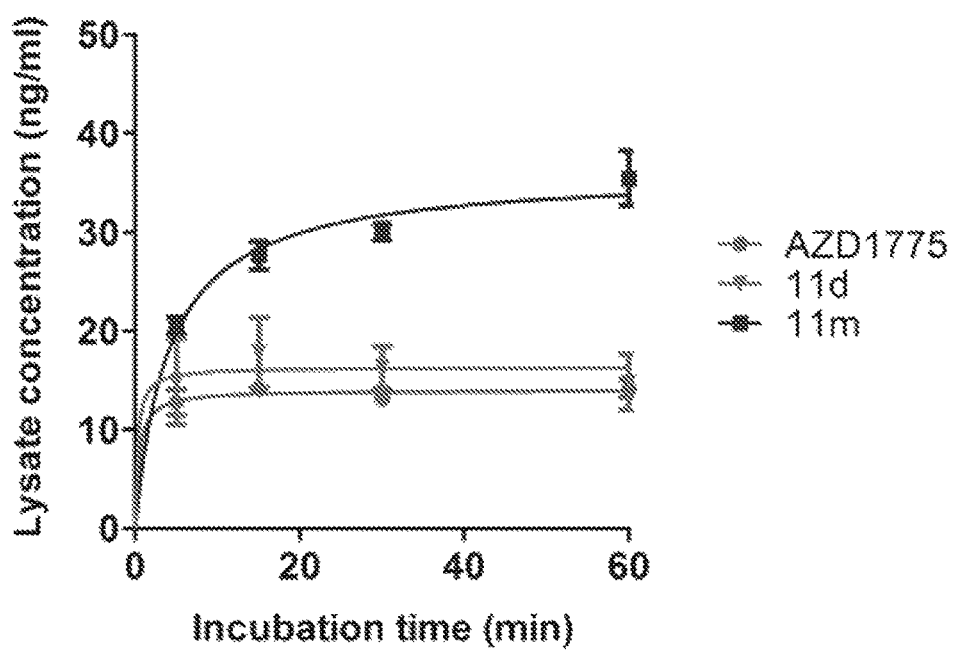
Figure 11E:
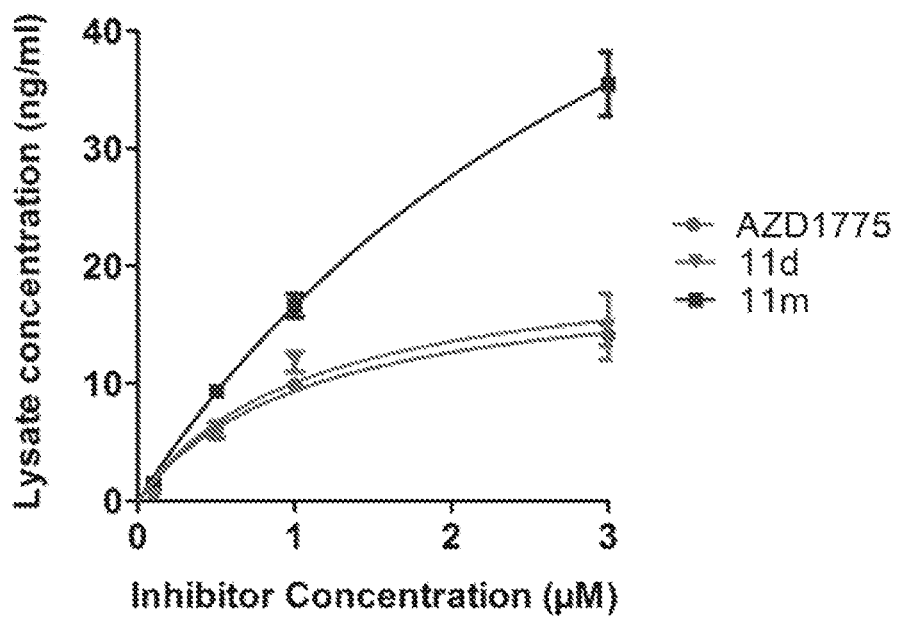

Wee1 inactivates CDC2 through selective phosphorylation of the Tyr5 residue of cyclin-dependent kinase 1 (CDK1) stabilizing the CDC2-cyclin B complex. Therefore, inhibition of Wee1 kinase activity will prevent the phosphorylation of its substrate CDK1 at Tyr15. To confirm the effect of our Wee1 inhibitors on downstream signaling, the inventors conducted immunoblotting analysis of phospho-CDK1 (Tyr5) levels in Daoy cell lysates following treatment with the Wee1 inhibitors AZD1775, 11a-d and 11m (FIG. 9A). Excluding 11c, all compounds reduced cellular pCDK1 in a dose-dependent manner. For a more quantitative analysis, an ELISA assay was utilized to determine the relative levels of pCDK1 (Tyr5) in Daoy cell lysates following treatment with a broader concentration range of AZD1775, 11d and 11m. Cellular pCDK1 levels were decreased to lower levels in the presence of AZD1775 versus comparable concentrations of 11d and 11m. Interpolation of the ELISA data determined that the concentrations of 11d and 11m necessary to result in the same level of cellular pCDK1 induced by 125 nM AZD1775 treatment were 205 nM and 565 nM, respectively (FIG. 9B). To evaluate the contribution of cellular pCDK1 (Tyr5) levels, and by extension, Wee1 activity, on the observed effects of Wee1 inhibitor treatment, the inventors repeated the real-time cell proliferation assay (xCELLigence) in Daoy cells over a broad concentration range of AZD1775, 11d and 11m for 76 hours (FIG. 10). AZD1775 mediated growth inhibition occurred between 62.5-125 nM, and this was greatly reduced with 11d (250 nM) and 11m (250-500 nM). However, as demonstrated with ELISA determination of pCDK1 (Tyr15) levels (FIG. 9B), AZD1775 reduces the cellular activity of Wee1 at lower concentrations than both 11d and 11m. To determine the contribution of cellular pCDK1 levels towards the inhibition of Daoy cell growth, the growth rate was plotted as a function of inhibitor concentration. Incubation with 125 nM AZD1775 resulted in a significantly reduced growth rate compared with vehicle control (0.033 vs. 0.068) (FIG. 10). In contrast, the functionally equivalent concentration of 205 nM 11d resulted in a nearly two-fold increase in the rate of cell growth compared with AZD1775 (0.063 vs. 0.033). For compound 11m, the equivalent concentration of 565 nM resulted in an even greater reduction in cell growth (0.012). Taken together, these data suggest that cellular pCDK1 levels, and as a result Wee1 activity, may not be the sole driving force behind the single agent growth inhibitory activity of AZD1775 and 11m.

Despite significant structural similarities between AZD1775, and compounds 11d and 11m all possessing cLogP values within acceptable limits (AZD1775; cLogP=2.18, 11d; cLogP=2.35, 11 m; cLogP=2.89), it was possible that differences in cellular permeability and retention could explain the differential effects of each Wee1 inhibitor on cell viability. Therefore, the inventors determined cellular uptake for AZD1775, 11d and 11m at varying concentrations and incubation times (FIG. 11). Surprisingly, there was little difference between cellular concentrations of AZD1775 and 11d, while 11m exhibited elevated levels at all concentrations and times.

Figure 12C:
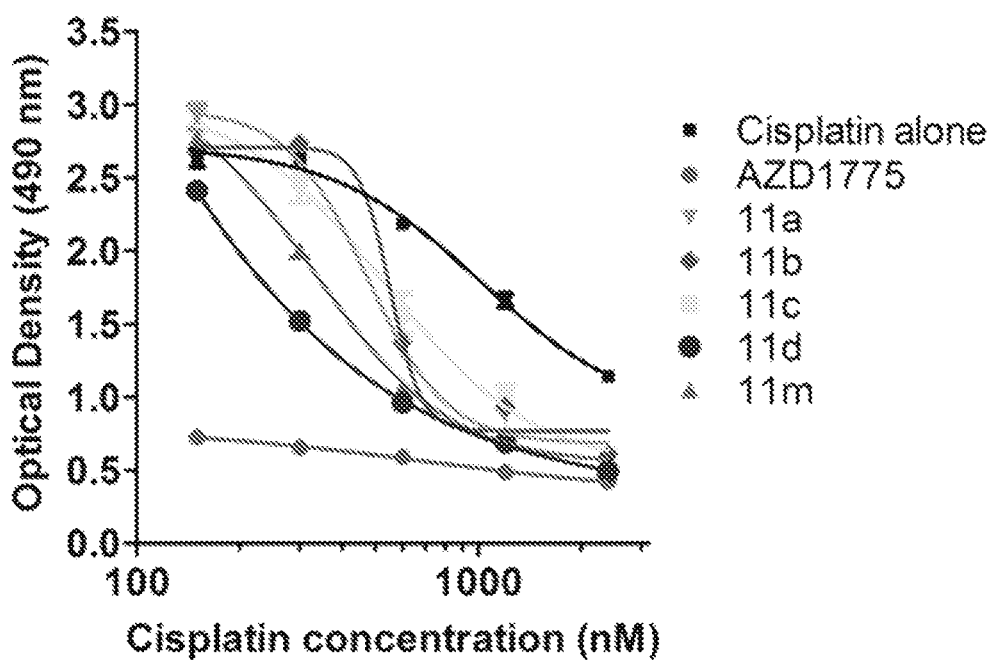
FIG. 12C shows the MTS assay in Daoy cells following treatment with Wee1 inhibitors and cisplatin for 72 hours. Dose responses for increasing cisplatin concentrations at a concentration (300 nM) of several Wee1 inhibitors, compared to cisplatin alone.
Figure 12A:
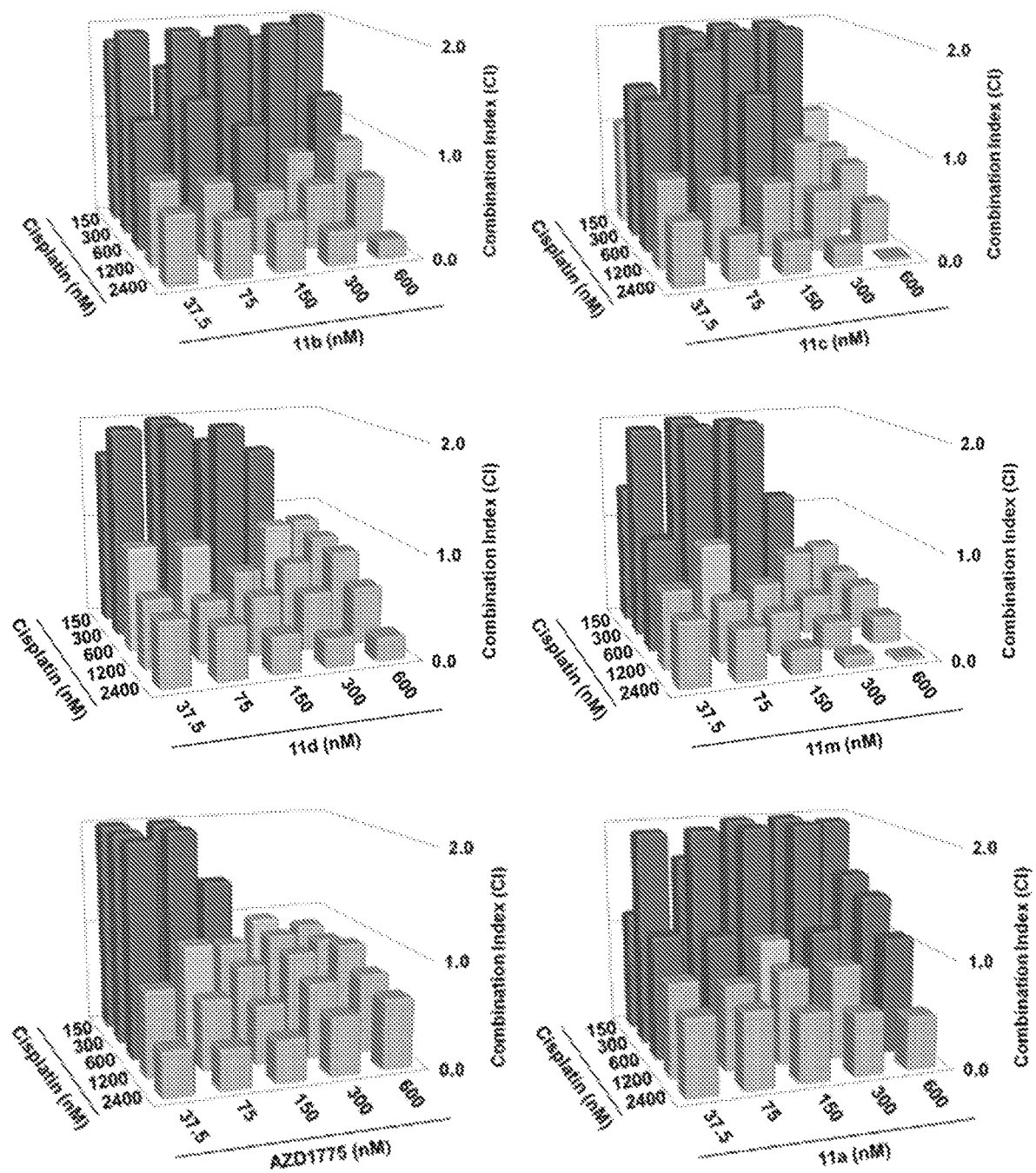

An MTS assay was used to determine Wee1 inhibitor synergy with the DNA-damaging agent cisplatin, which is an expected outcome in response to Wee1 inhibition. Daoy cells were treated for 72 hours with increasing concentrations of both cisplatin and Wee1 inhibitor (AZD1775, 11a-d or 11m) and the effects of drug combinations were analyzed using the Chou-Talalay equation. The Combinatorial Index (CI) was determined for each drug combination. A CI value <1 indicates a synergistic effect, whereas a CI of >1 indicates a non-synergistic effect. As expected, AZD1775 showed strong synergy with cisplatin across all concentrations except the lowest cisplatin and Wee1 inhibitor concentrations (FIGS. 12A and 12B). All of the Wee1 inhibitors (11a-d, 11m) exhibited synergy with cisplatin particularly at higher concentrations of cisplatin. The potent Wee1 inhibitors 11d and 11m exhibited synergistic activity at lower cisplatin concentrations and were more comparable with AZD1775. In particular, at 600 nM cisplatin, synergy was observed across all concentrations of 11d and all but the lowest concentration of 11m, indicating an improvement over the synergy profile of AZD1775. Dose-response curves from the MTS assay were plotted for cisplatin as a single agent and when paired with a single concentration of Wee1 inhibitor (FIG. 12C). A concentration of 300 nM was chosen for the Wee1 inhibitors as no effect was observed in Daoy cells treated with Wee1 inhibitor alone at this concentration in all cases except AZD1775. When compared with cisplatin treatment, co-treatment with our inhibitors potentiated the effect of cisplatin. The effect was also potentiated in the presence of AZD1775, but this was due to the extensive loss of cellular viability in the presence of AZD1775 alone at this concentration. Interestingly, when the treatments were repeated using AZD1775, 11d and 11m in combination with cisplatin in p53 wild-type ONS-76 cells, similar results were observed. These data support previous studies suggesting that Wee1 inhibition acts in synergy with DNA damage independent of cellular p53 status.

Figure 13A:
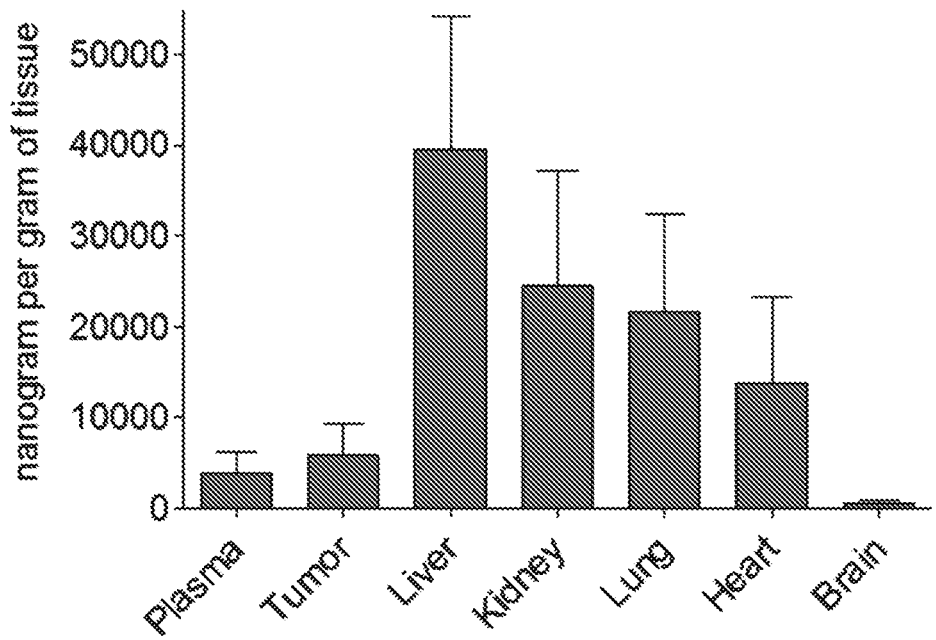
FIGS. 13A and 13B show the tissue distribution of AZD1775.
Figure 13B:
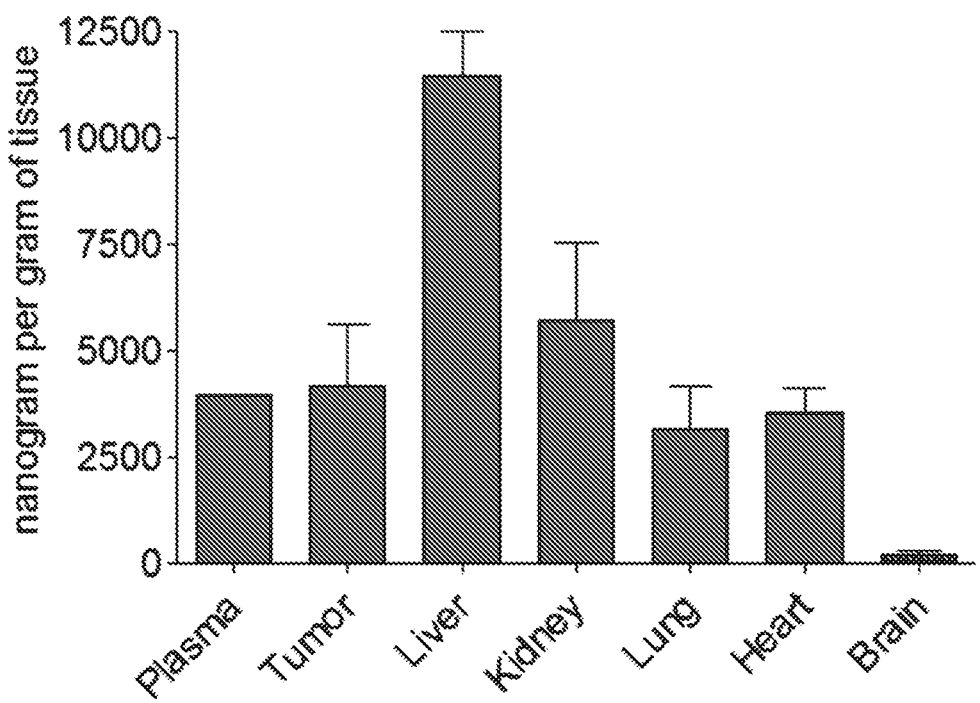

The pharmacokinetics (PKs) and tissue distribution of AZD1775 and Wee1 inhibitors was examined in mice. In dorsal flank tumor xenografts the inventors established to determine the effect of Wee1 inhibitors as single agents, the inventors found that trace amounts of AZD1775 or 11d penetrated the brain (FIG. 13).

Example 5: Synthesis of Inhibitors

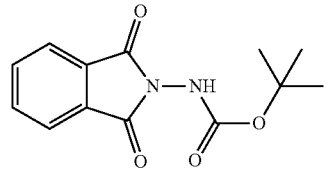 [SMILES: CC(C)(C)OC(=O)NN1C(=O)c2ccccc2C1=O]

Synthesis of tert-butyl (1,3-dioxoisoindolin-2-yl)carbamate (3)

tert-Butyl carbazate (2; 9.40 g, 70.9 mmol) was added portionwise to a solution of phthalic anhydride (1; 10.0 g, 67.5 mmol) in refluxing toluene (110 ml). The resultant suspension was heated under reflux conditions for 18 h, before being cooled and the precipitate removed by filtration. The filtrand was washed with hexanes and dried under vacuum to give the desired product as a white crystalline solid (16.1 g, 61.4 mmol, 91%). Rf 0.68 (1:1 Hexane:EtOAc); M.p. 191-194° C. (Lit.=186° C.); (1) IR (cm-1) 3316, 2979, 1796, 1730, 1614, 1490; 1H NMR (400 MHz, DMSO-d6) 1.45 (9H, s, —OC(CH3)3), 7.87-8.04 (4H, m, H-4/5/6/7), 9.86 (1H, s, NH); 13C NMR (125 MHz, DMSO-d6) 28.3 (C(CH3)3), 81.6 (C(CH3)3), 124.2 (Ar—C), 129.8 (Ar—C), 135.8 (Ar—C), 154.4 (C=O), 165.9 (C=O).

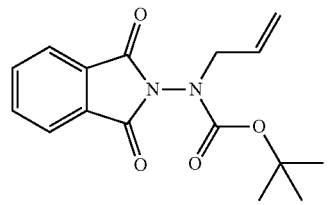 [SMILES: C=CCN(C(=O)OC(C)(C)C)N1C(=O)c2ccccc2C1=O]

Synthesis of tert-butyl allyl(1,3-dioxoisoindolin-2-yl)carbamate (4)

Potassium carbonate (16.1 g, 116 mmol), benzyltriethylammonium chloride (1.39 g, 6.12 mmol) and allyl bromide (8.00 ml, 91.8 mmol) were added sequentially to a suspension of carbamate 3 (16.1 g, 61.2 mmol) in acetonitrile (110 ml). The reaction mixture was stirred at RT for 18 h, before water (100 ml) was added. The organic extract was evaporated to dryness and the resultant pale yellow oil was triturated with hexanes and cooled to 5° C. The precipitate was removed via filtration and washed with hexanes to afford the desired product as a white crystalline solid (15.7 g, 52.1 mmol, 85%). Rf 0.52 (4:1 Hexane:EtOAc); M.p. 72-75° C. (Lit.=76-78° C.); (1) IR (cm-1) 2978, 2936, 1792, 1719, 1641; 1H NMR (400 MHz, DMSO-d6) 1.25 & 1.46 (9H, s, C(CH3)3), 4.19 (2H, dapp, J=6.1 Hz, N—CH2), 5.10-5.17 (1H, m, allyl C-Htrans), 5.27 (1H, dd, J=17.3, 1.3 Hz, allyl C-Hcis), 5.78-5.93 (1H, m, allyl C—H), 7.93-8.02 (4H, m, H-4/5/6/7); 13C NMR (125 MHz, DMSO-d6) 27.9

(C(CH3)3), 28.1 (C(CH3)3), 51.7 31 (N—CH2), 53.7 (N—CH2), 82.1 (C(CH3)3), 82.8 (C(CH3)3), 119.1 (allyl-CH2), 119.7 (allyl-CH2), 124.3, 124.4, 129.5, 129.6, 132.8 (Ar—C), 133.3 (Ar—C), 135.9 (Ar—C), 136.0 (Ar—C), 153.0 (C=O), 153.1 (C=O), 165.3 (C=O), 165.5 (C=O).

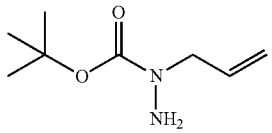

Synthesis of tert-butyl 1-allylhydrazine-1-carboxylate (5)

Methylhydrazine (3.40 ml, 64.3 mmol) was added to an ice cooled solution of phthalamide 4 (15.6 g, 51.5 mmol) in THF (100 ml). The reaction mixture was allowed to warm to RT and was stirred for 18 h. The resultant white suspension was passed through a filter, and the filtrate was concentrated in vacuo. A mixture of Hexanes:EtOAc (3:1) was added, and the precipitate formed was removed via filtration. This process was repeated a further 2 times, and the final filtrate was concentrated to give the target compound as a pale yellow oil (8.47 g, 49.2 mmol, 96%). Rf 0.22 (4:1 Hexane:EtOAc); IR (cm-1) 3336, 2977, 2932, 1690; 1H NMR (400 MHz, DMSO-d6) 1.40 (9H, s, —C(CH3)3), 3.85 (2H, ddd, J=5.5, 1.4, 1.4 Hz, N—CH2), 4.46 (2H, s, NH2), 5.06-5.09 (1H, m, allyl C-Htrans), 5.11 (1H, br, allyl C-Hcis), 5.74-5.86 (1H, m, allyl C—H); 13C NMR (125 MHz, DMSO-d6) 28.5 (C(CH3)3), 53.6 (N—CH2), 79.4 (C(CH3)3), 116.2 (allyl-CH2), 134.6 (allyl-CH), 156.5 (C=O).

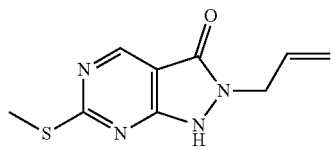

Synthesis of 2-allyl-6-(methylthio)-1,2-dihydro-3H-pyrazolo[3,4-d]pyrimidin-3-one (7)

DIPEA (20.8 ml, 120 mmol) and allylhydrazine 5 (8.23 g, 47.8 mmol) were added to a solution of ethyl 4-chloro-2-methylthio-5-pyrimidinecarboxylate (6; 11.1 g, 47.8 mmol) in THF (150 ml). The reaction mixture was heated at reflux for 72 h, before being concentrated in vacuo. Et2O (50 ml) was added to the residue, and the resultant precipitate was collected by filtration. The filtrate was evaporated to dryness, and the residue was cooled in an ice bath, after which TFA (40 ml) was added. The resultant solution was stirred at RT for 1 h, followed by 70° C. for 1 h. The solvent was removed in vacuo and the residue was dissolved in EtOH (50 ml) and cooled in an ice bath, after which 6M NaOH (75 ml) was added. The resultant solution was stirred at RT for 15 min, before 32 being acidified via the addition of conc. HCl (40 ml). The orange solution was evaporated to dryness and the resultant residue was partitioned between chloroform (100 ml) and water (100 ml), and the organic phase was washed with brine (50 ml), dried (Mg2SO4), concentrated in vacuo, and triturated with hexanes. The solid precipitate was washed with EtOH and Et2O, before being dried under vacuum to give the target compound as a yellow solid (5.44 g, 24.5 mmol, 51%). Rf 0.45 (9:1 DCM:MeOH); M.p. 125-128° C.; IR (cm-1) 3032, 2979, 2926, 2659, 1656, 1615, 1566, 1514; 1H NMR (400 MHz, DMSO-d6) 2.53 (3H, s, —SCH3), 4.38 (2H, dapp, J=5.2 Hz, N2-CH2), 5.06-5.20 (2H, m, allyl C-Hcis/trans), 5.87 (1H, ddt, J=17.2, 10.5, 5.3 Hz, alkene C—H), 8.67 (1H, s, H-4), 12.65 (1H, br, H-1); MS [M+H]+m/z 223.1.

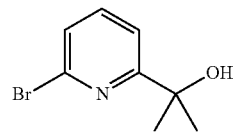

Synthesis of 2-(6-bromopyridin-2-yl)propan-2-ol (8a)

Methylmagnesium iodide (3M in Et2O, 1.50 ml, 4.48 mmol) was added to a solution of methyl 6-bromopyridine-2-carboxylate (0.430 g, 1.99 mmol) in dry Et2O (15 ml) under N2. After 5 min at RT the reaction was quenched with 1M HCl (10 ml) and extracted with EtOAc (15 ml). The organic extract was washed with sat. NaHCO3 solution (15 ml) and brine (10 ml), dried (MgSO4) and concentrated in vacuo. The desired product was obtained as a yellow oil (0.365 g, 1.69 mmol, 85%). Rf 0.60 (1:1 Hexane:EtOAc); IR (cm-1) 3420, 2975, 2930, 1731, 1701, 1580, 1553; 1H NMR (400 MHz, DMSO-d6) 1.42 (6H, s, C(CH2)2), 5.33 (1H, s, OH), 7.47 (1H, dd, J=7.7, 0.9 Hz, H-5), 7.67 (1H, dd, J=7.7, 0.9 Hz, H-3), 7.73 (1H, dd, J=7.7, 7.7 Hz, H-4); 13C NMR (125 MHz, DMSO-d6) 30.9 (C(CH2)2), 72.6 (C(CH2)2), 118.5 (Ar—C), 126.0 (Ar—C), 140.4 (Ar—C), 140.5 (Ar—C), 170.8 (Ar—C).

General Method for the Preparation of Pyridyl Pyrazolopyrimidinones (9a-c)

N,N'-Dimethylethylenediamine (4.47 mmol) was added to a solution of pyrazolopyrimidine 7 (2.25 mmol), bromopyridine (8a-c; 2.93 mmol), copper iodide (2.25 mmol) and K2CO3 (3.15 mmol) in 1,4-dioxane (5 ml) at 80° C. The resultant suspension was heated at 95° C. for 18 h, over which time a colour change of orange to dark green occurred. The reaction mixture was cooled to RT and diluted with NH4OH (10 ml) before being extracted with EtOAc (2×20 ml). The combined organic extracts were washed with brine (20 ml), dried 33 (MgSO4) and evaporated to dryness. The crude material was purified via silica gel chromatography (19:1 DCM:MeOH) to afford the target pyridyl pyrazolopyrimidinones (69-84%).

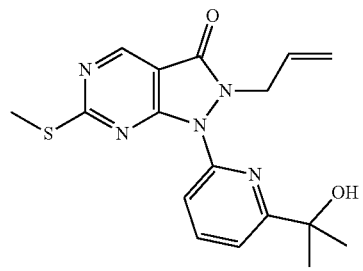 [SMILES: C=CCn1c(=O)c2cnc(SC)nc2n1-c1cccc(C(C)(C)O)n1]

2-Allyl-1-(6-(2-hydroxypropan-2-yl)pyridin-2-yl)-6-(methylthio)-1,2-dihydro-3H-pyrazolo[3,4-d]pyrimidin-3-one (9a)

Rf 0.63 (9:1 DCM:MeOH); M.p. 108-111° C.; IR (cm-1) 3337, 3081, 2966, 2924, 1663, 1601, 1559; 1H NMR (400 MHz, CDCl3) 1.61 (6H, s, C(CH3)2), 2.61 (3H, s, S—CH3), 3.77 (1H, s, —OH), 4.82 (2H, dapp, J=5.9 Hz, N2-CH2), 4.95 (1H, dapp, J=16.9 Hz, allyl C-Htrans), 5.08 (1H, dapp, J=10.3 Hz, allyl C-Hcis), 5.72 (1H, ddt, J=16.9, 10.3, 5.9 Hz, allyl C—H), 7.42 (1H, d, J=7.7 Hz, H-5'), 7.78 (1H, d, J=8.0 Hz, H-3'), 7.93 (1H, dd, J=8.0, 7.7 Hz, H-4'), 8.96 (1H, s, H-4); 13C NMR (125 MHz, CDCl3) 14.5 (SCH3), 30.5 (C(CH3)2), 47.5 (N2-CH2), 72.5 (C(CH3)2), 116.4 (Ar—C), 116.6 (Ar—C), 119.3 (allyl-CH2), 131.2, 139.2, 147.0 (Ar—C), 154.3 (Ar—C), 159.2 (C=O), 161.0 (Ar—C), 166.1 (Ar—C), 177.0 (Ar—C); MS [M+H]+m/z 359.3.

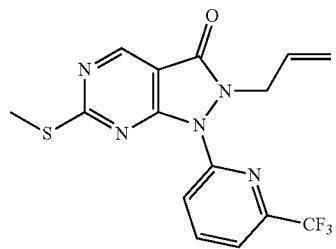 [SMILES: C=CCn1c(=O)c2cnc(SC)nc2n1-c1cccc(C(F)(F)F)n1]

2-Allyl-6-(methylthio)-1-(6-(trifluoromethyl)pyridin-2-yl)-1,2-dihydro-3H-pyrazolo[3,4-d]pyrimidin-3-one (9b)

Rf 0.56 (19:1 EtOAc:MeOH); M.p. 99-102° C.; IR (cm-1) 3076, 2929, 2330, 1692, 1599, 1558; 1H NMR (400 MHz, CDCl3) 2.64 (3H, s, S—CH3), 4.92-5.05 (4H, m, N2-CH2 & allyl C-Htrans), 5.03 (1H, dapp, J=9.9 Hz, allyl C-Hcis), 5.69 (1H, ddt, J=16.8, 9.9, 6.8 Hz, allyl C—H), 7.63 (1H, d, J=7.6 Hz, H-5'), 8.08 (1H, dd, J=8.1, 7.6 Hz, H-4'), 8.29 (1H, d, J=8.1 Hz, H-3'), 8.98 (1H, s, H-4); 13C NMR (125 MHz, DMSO-d6) 14.5 (SCH3), 47.9 (N2-CH2), 104.9 (Ar—C), 119.0 (q, JCF=2.8 Hz, Ar—C), 119.3 (allyl-CH2), 121.6 (q, JCF=34 274.2 Hz, CF3), 121.7 (Ar—C), 132.3, 141.7 (Ar—C), 145.2 (q, JCF=34.7 Hz, Ar—C), 148.7 (Ar—C), 155.2 (Ar—C), 159.2 (C=O), 161.0 (Ar—C), 176.6 (Ar—C); MS [M+H]+m/z 368.1.

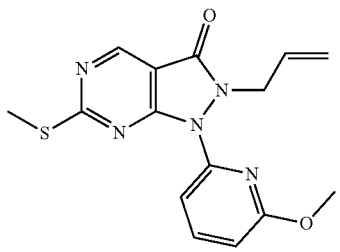

2-Allyl-1-(6-methoxypyridin-2-yl)-6-(methylthio)-1,2-dihydro-3H-pyrazolo[3,4-d]pyrimidin-3-one (9c)

Rf 0.44 (19:1 EtOAc:MeOH); M.p. 114-116° C.; IR (cm-1) 3096, 3056, 2989, 2927, 2356, 1705, 1599, 1557; 1H NMR (400 MHz, CDCl3) 2.59 (3H, s, SCH3), 3.95 (3H, s, OCH3), 4.87 (2H, dapp, J=6.1 Hz, N2-CH2), 4.99 (1H, dapp, J=16.8 Hz, allyl C-Htrans), 5.08 (1H, dapp, J=10.3 Hz, allyl C-Hcis), 5.72 (1H, ddt, J=16.8, 10.3, 6.1 Hz, allyl C—H), 6.73 (1H, d, J=8.2 Hz, H-5'), 7.42 (1H, d, J=7.7 Hz, H-3'), 7.78 (1H, dd, J=8.2, 7.7 Hz, H-4'), 8.95 (1H, s, H-4); 13C NMR (125 MHz, DMSO-d6) 14.4 (SCH3), 47.1 (N2-CH2), 54.2 (OCH3), 104.6 (Ar—C), 109.2 (Ar—C), 111.5 (Ar—C), 118.9 (allyl-CH2), 132.3, 141.9 (Ar—C), 146.0 (Ar—C), 154.9, 158.8, 160.4 (Ar—C), 163.3 (Ar—C), 176.2 (Ar—C); MS [M+H]+m/z 330.2.

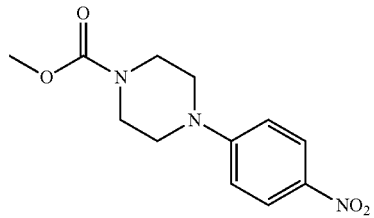

Synthesis of methyl 4-(4-nitrophenyl)piperazine-1-carboxylate (12)

K2CO3 (1.34 g, 9.66 mmol) and methyl chloroformate (0.56 ml, 7.24 mmol) were added to a solution of 1-(4-nitrophenyl)piperazine (1.00 g, 4.83 mmol) in DCM (20 ml). The solution was stirred at RT for 30 min before 1M NaOH (15 ml) was added and the mixture was extracted with DCM (2×20 ml). The combined organic extracts were washed with brine (20 ml), dried (MgSO4) and concentrated in vacuo to give the target compound as a yellow solid (1.24 g, 4.67 mmol, 97%). Rf 0.32 (1:1 Hexanes:EtOAc); M.p. 166-168° C.; IR (cm-1) 2953, 2904, 2854, 2364, 1692, 1588; 1H NMR (400 MHz, DMSO-d6) 3.50-3.53 (8H, br, N(CH2CH2)2NCO), 3.64 (3H, s, CO2CH3), 7.02 (2H, d, J=9.5 Hz, H-2/6), 8.08 (2H, d, J=9.5 Hz, H-3/5); 13C NMR (125 MHz, DMSO-d6) 43.2 (NCH2), 46.4 (NCH2), 52.9 (OCH3), 113.1 (Ar—C), 126.2 (Ar—C), 137.5 (Ar—C), 154.9, 155.5.

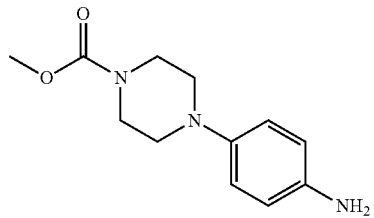 [SMILES: COC(=O)N1CCN(c2ccc([N+](=O)[O-])cc2)CC1]

Synthesis of methyl 4-(4-aminophenyl)piperazine-1-carboxylate (10e)

Palladium on carbon (0.11 g, 10% w/w) and ammonium formate (2.64 g, 41.8 mmol) were added to a solution of nitro aromatic 12 (1.11 g, 4.18 mmol) in MeOH (40 ml). The reaction mixture was stirred at RT for 18 h before being filtered through celite, evaporated to dryness and redissolved in EtOAc (100 ml). The organic phase was washed with water (100 ml) and brine (50 ml) before being dried (MgSO4) and concentrated in vacuo to give the desired compound as a pale pink solid (0.897 g, 3.81 mmol, 91%). Rf 0.19 (1:1 Hexanes:EtO); M.p. 130-133° C.; IR (cm-1)

3429, 3352, 3017, 2952, 2915, 3814, 2748, 2359, 1682, 1624, 1606, 1515; 1H NMR (400 MHz, DMSO-d6) 2.83-2.88 (4H, m, N(CH2CH2)2NCO), 3.45-3.50 (4H, m, N(CH2CH2)2NCO), 3.62 (3H, s, CO2CH3), 4.62 (2H, br, C4-NH2), 6.50 (2H, d, J=8.6 Hz, H-3/5), 6.70 (2H, d, J=8.6 Hz, H-2/6); 13C NMR (125 MHz, DMSO-d6) 44.1 (NCH2), 51.1 (NCH2), 52.8 (OCH3), 115.1 (Ar—C), 119.2 (Ar—C), 142.6 (Ar—C), 143.3 (Ar—C), 155.5 (C=O); MS [M+H]+ m/z 235.2.

General Method for the Preparation of Aniline Pyridyl Pyrazolopyrimidinones (11a-n).

mCPBA (0.34 mmol) was added to a solution of pyrazolopyrimidinones 9a-c (0.31 mmol) in toluene (5 ml) and the resulting mixture was stirred at RT for 1 h. DIPEA (1.63 mmol) and the relevant substituted aniline 10a-e (0.40 mmol) were added, and the reaction mixture was stirred at RT for 18 h. Saturated NaHCO3 solution (15 ml) was added, and the mixture was extracted with EtOAc (2×15 ml). The combined organic extracts were washed with brine (10 ml), dried (MgSO4) and concentrated in vacuo. The resultant residue was purified via chromatography on silica (19:1 DCM:MeOH) to give the target compound as a yellow solid (55-72%).

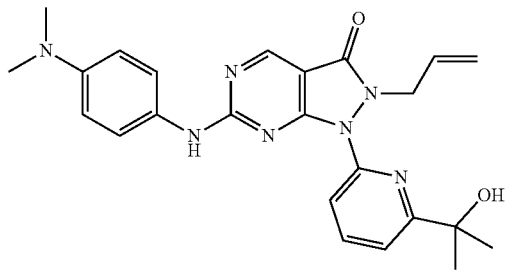 [SMILES: C=CCn1c(=O)c2cnc(Nc3ccc(N(C)C)cc3)nc2n1-c1cccc(C(C)(C)O)n1]

2-Allyl-6-((4-(dimethylamino)phenyl)amino)-1-(6-(2-hydroxypropan-2-yl)pyridin-2-yl)-1,2-dihydro-3Hpyrazolo[3,4-d]pyrimidin-3-one (11a)

Rf 0.37 (19:1 DCM:MeOH); M.p. 173-175° C.; IR (cm-1) 3325, 3245, 3172, 3056, 2964, 2922, 2357, 1669, 1611, 1568, 1542, 1516; 1H NMR (400 MHz, DMSO-d6) 1.47 (6H, s, C(CH3)2), 2.88 (6H, s, N(CH3)2), 4.68 (2H, dapp, J=6.0 Hz, N2-CH2), 4.83 (1H, dapp, J=17.2 Hz, allyl CHtrans), 5.00 (1H, dapp, J=10.1 Hz, allyl C-Hcis), 5.32 (1H, s, OH), 5.67 (1H, ddt, J=17.2, 10.1, 6.0 Hz, allyl C—H), 6.73 (2H, d, J=8.6 Hz, H-3"/5"), 7.49-7.57 (1H, m, H-5'), 7.60 (2H, d, J=8.6 Hz, H-2"/6"), 7.76 (1H, dapp, J=7.3 Hz, H-5'), 8.03 (1H, dd, J=7.6, 7.5 Hz, H-4'), 8.81 (1H, s, H-4), 10.08 (1H, br, C6-NH); 13C NMR (125 MHz, DMSO-d6) 30.9 (C(CH3)2), 41.0 (N(CH3)2), 47.1 (N2-CH2), 72.8 (C(CH3)2), 113.0, 116.0, 116.7, 118.7, 122.1, 129.0, 132.7, 139.2, 147.5, 156.4, 161.1, 161.5, 161.8, 168.0; MS [M+H]+ m/z 446.3.

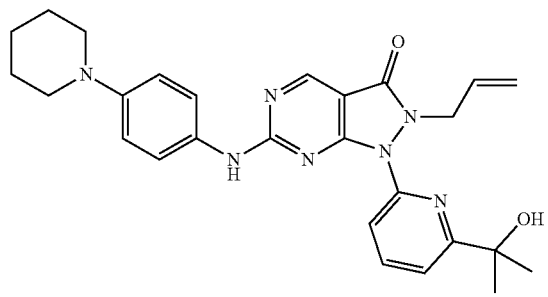 [SMILES: C=CCn1c(=O)c2cnc(Nc3ccc(N4CCCCC4)cc3)nc2n1-c1cccc(C(C)(C)O)n1]

2-Allyl-1-(6-(2-hydroxypropan-2-yl)pyridin-2-yl)-6-((4-(piperidin-1-yl)phenyl)amino)-1,2-dihydro-3Hpyrazolo[3,4-d]pyrimidin-3-one (11b)

Rf 0.38 (19:1 DCM:MeOH); M.p. 158-160° C.; IR (cm-1) 3267, 2928, 2851, 2790, 2360, 1668, 1606, 1567, 1532, 1508; 1H NMR (400 MHz, DMSO-d6) 1.47 (6H, s, C(CH3)2), 1.50-1.56 (2H, m, N(CH2CH2CH)2), 1.59-1.68 (4H, m, N(CH2CH2CH)2), 3.06-3.11 (4H, m, N(CH2CH2CH)2), 4.68 (2H, dapp, J=5.8 Hz, N2-CH2), 4.83 (1H, dapp, J=17.3 Hz, allyl C-Htrans), 5.00 (1H, dapp, J=10.1 Hz, allyl CHcis), 5.33 (1H, s, OH), 5.67 (1H, ddt, J=17.2, 10.1, 5.8 Hz, allyl C—H), 6.92 (2H, d, J=8.7 Hz, H-3"/5"), 7.53-7.59 (1H, m, H-5'), 7.61 (2H, d, J=8.7 Hz, H-2"/6"), 7.76 (1H, dapp, J=7.9 Hz, H-5'), 8.02-8.08 (1H, m, H-4'), 8.83 (1H, s, H-4), 10.14 (1H, br, C6-NH); 13C NMR (125 MHz, DMSO-d6) 24.3 (piperidine-CH2), 25.8 (piperidine-CH2), 30.9 (C(CH3)2), 47.1 (N2-CH2), 50.6 (piperidine-CH2), 72.8 (C(CH3)2), 116.5, 116.7, 118.7, 121.7, 131.0, 132.7, 139.3, 147.6, 148.4, 156.5, 161.0, 161.7, 168.0; MS [M+H]+m/z 486.4.

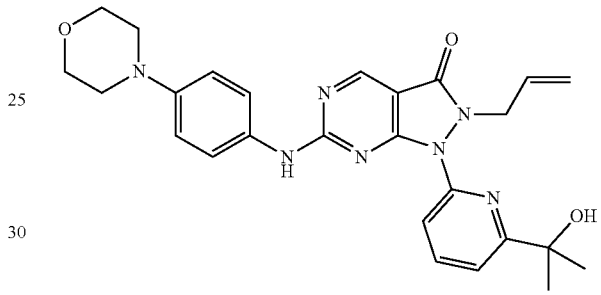

2-Allyl-1-(6-(2-hydroxypropan-2-yl)pyridin-2-yl)-6-((4-morpholinophenyl)amino)-1,2-dihydro-3Hpyrazolo[3,4-d]pyrimidin-3-one (11c)

Rf 0.40 (19:1 DCM:MeOH); M.p. 200-203° C.; IR (cm-1) 3383, 2969, 2858, 2813, 2358, 1659, 1609, 1565, 1525, 1510; 1H NMR (400 MHz, DMSO-d6) 1.47 (6H, s, C(CH3)2), 3.05-3.11 (4H, br, N(CH2CH2)2O), 3.73-3.78 (4H, br, N(CH2CH2)2O), 4.69 (2H, dapp, J=5.9 Hz, N2-CH2), 4.83 (1H, dd, J=17.1, 1.3 Hz, allyl C-Htrans), 5.00 (1H, dd, J=10.2, 1.3 Hz, allyl C-Hcis), 5.33 (1H, s, OH), 5.67 (1H, ddt, J=17.1, 10.2, 5.9 Hz, allyl C—H), 6.94 (2H, d, J=9.0 Hz, H-3/5"), 7.57-7.61 (1H, m, H-5'), 7.61 (2H, d, J=9.0 Hz, H-2/6"), 7.76 (1H, dapp, J=8.1 Hz, H-3'), 8.05 (1H, dd, J=7.9, 7.2 Hz, H-4'), 8.84 (1H, s, H-4), 10.17 (1H, br, C6-NH); 13C NMR (125 MHz, DMSO-d6) 30.9 (C(CH3)2), 47.1 (N2-CH2), 49.4 (N(CH2CH2)2O), 66.6 (N(CH2CH2)2O), 72.8 (C(CH3)2), 115.7, 116.1, 116.8, 118.7, 121.7, 131.6, 132.7, 139.3, 147.6, 156.5, 161.0, 161.5, 161.6, 168.1; MS [M+H]+m/z 488.3.

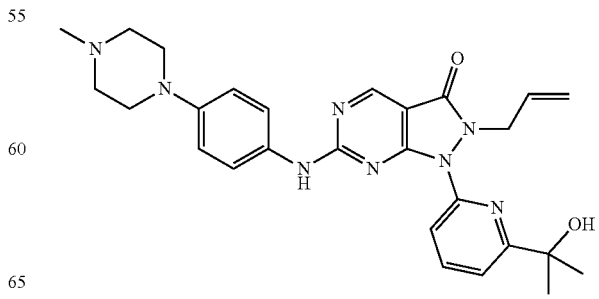

2-Allyl-1-(6-(2-hydroxypropan-2-yl)pyridin-2-yl)-6-((4-(4-methylpiperazin-1-yl)phenyl) amino)-1,2-dihydro-3H-pyrazolo[3,4-d]pyrimidin-3-one (AZD1775)

Rf 0.25 (9:1 DCM:MeOH); M.p. 170-174° C.; IR (cm-1) 3420, 2969, 2810, 2364, 1639, 1602, 1541, 1512; 1H NMR (400 MHz, DMSO-d6) 1.47 (6H, s, C(CH3)2), 2.23 (3H, s, N—CH3), 2.42-2.50 (4H, m, N—(CH2CH2)2-NMe), 3.05-3.14 (4H, m, N—CH2CH2-NMe), 4.69 (2H, dapp, J=5.9 Hz, N2-CH2), 4.83 (1H, dd, J=17.1, 1.3 Hz, alkene C-Htrans), 5.00 (1H, dd, J=10.3, 1.3 Hz, alkene C-Hcis), 5.32 (1H, s, —OH), 5.67 (1H, ddt, J=17.1, 10.3, 5.9 Hz, alkene C—H), 6.93 (2H, d, J=9.1 Hz, H-3/5"), 7.54-7.60 (1H, m, H-5'), 7.61 (2H, d, J=9.1 Hz, H-2/6"), 7.76 (1H, dapp, J=8.1 Hz, H-3'), 8.06 (1H, dd, J=8.1, 7.3 Hz, H-4'), 8.83 (1H, s, H-4), 10.1 (1H, br, C6-NH); 13C NMR (125 MHz, DMSO-d6) 30.9 (C(CH3)2), 46.2 (N—CH3), 47.1 (N2-CH2), 48.9 (piperazine-CH2), 55.1 (piperazine-CH2), 72.8 (C(CH3)2), 116.0, 116.7, 118.7, 121.6, 131.3, 132.7, 139.3, 147.6, 156.5, 161.0, 161.6, 168.0; MS [M+H]+m/z 501.4.

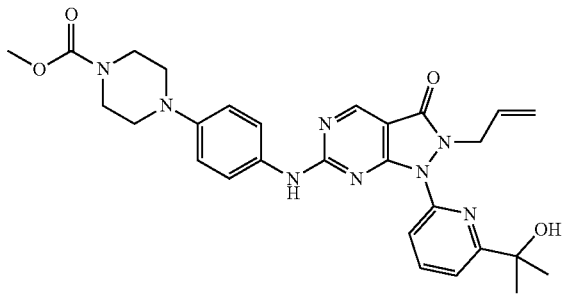 [SMILES: C=CCn1c(=O)c2cnc(Nc3ccc(N4CCN(C(=O)OC)CC4)cc3)nc2n1-c1cccc(C(C)(C)O)n1]

Methyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate (11d)

Rf 0.41 (19:1 DCM:MeOH); M.p. 201-204° C.; IR (cm-1) 3409, 3383, 2957, 2865, 2820, 2357, 1697, 1678, 1608, 1568, 1522; 1H NMR (400 MHz, DMSO-d6) 1.47 (6H, s, C(CH3)2), 3.05-3.11 (4H, m, N(CH2CH2)2NCO), 3.49-3.55 (4H, m, N(CH2CH2)2NCO), 3.64 (3H, s, CO2CH3), 4.69 (2H, dapp, J=5.9 Hz, N2-CH2), 4.83 (1H, dapp, J=17.1 Hz, allyl C-Htrans), 5.00 (1H, dapp, J=10.3 Hz, allyl C-Hcis), 5.33 (1H, s, OH), 5.67 (1H, ddt, J=17.0, 10.4, 5.9 Hz, allyl C—H), 6.96 (2H, d, J=8.5 Hz, H-3"/5"), 6.57-6.64 (3H, m, H-5'/2"/6"), 7.76 (1H, dapp, J=8.2 Hz, H-3'), 8.02-8.08 (1H, m, H-4'), 8.84 (1H, s, H-4), 10.17 (1H, br, C6-NH); 13C NMR (125 MHz, DMSO-d6) 30.9 (C(CH3)2), 43.8 (piperazine-CH2), 47.1 (N2-CH2), 49.4 (piperazine-CH2), 52.8 (OCH3), 72.8 (C(CH3)2), 116.2, 116.8, 118.7, 121.7, 132.0, 132.7, 139.3, 147.4, 147.5, 155.5, 156.5, 160.9, 161.4, 161.6, 168.1; MS [M+H]+m/z 545.4.

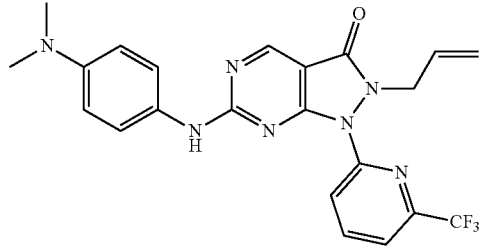 [SMILES: C=CCn1c(=O)c2cnc(Nc3ccc(N(C)C)cc3)nc2n1-c1cccc(C(F)(F)F)n1]

2-Allyl-6-((4-(dimethylamino)phenyl)amino)-1-(6-(trifluoromethyl)pyridin-2-yl)-1,2-dihydro-3Hpyrazolo[3,4-d]pyrimidin-3-one (11e)

Rf 0.57 (19:1 DCM:MeOH); M.p. 179-181° C.; IR (cm-1) 3255, 3178, 3079, 2794, 2358, 1685, 1621, 1594, 1567, 1517; 1H NMR (400 MHz, DMSO-d6) 2.89 (6H, s, N(CH3)2), 4.66 (2H, dapp, J=6.1 Hz, N2-CH2), 4.88 (1H, dapp, J=17.2 Hz, allyl C-Htrans), 5.01 (1H, dapp, J=10.0 Hz, allyl CHcis), 5.70 (1H, ddt, J=17.2, 10.0, 6.1 Hz, allyl C—H), 6.76 (2H, d, J=7.9 Hz, H-3"/5"), 7.52 (2H, d, J=7.9 39 Hz, H-2"/6"), 7.85 (1H, dapp, J=7.2 Hz, H-5'), 8.24-8.35 (2H, m, H-3'/4'), 8.85 (1H, s, H-4), 10.21 (1H, br, C6-NH); 13C NMR (125 MHz, DMSO-d6) 40.9 (N(CH3)2), 48.0 (N2-CH2), 112.9, 118.3, 119.2, 121.2, 121.7 (q, JCF=273.8 Hz, CF3), 122.4 (q, JCF=4.8 Hz, Ar—C), 128.7, 132.5, 141.1, 145.1 (q, JCF=35.4 Hz, Ar—C), 147.7, 149.4, 156.7, 161.6, 161.8, 162.5; MS [M+H]+m/z 456.2.

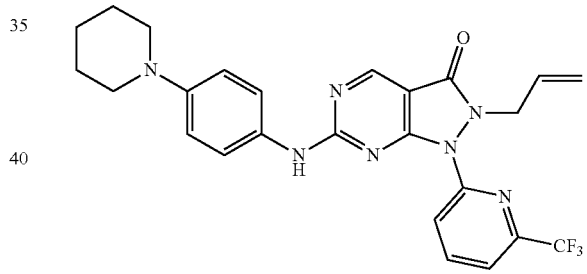

2-Allyl-6-((4-(piperidin-1-yl)phenyl)amino)-1-(6-(trifluoromethyl)pyridin-2-yl)-1,2-dihydro-3Hpyrazolo[3,4-d]pyrimidin-3-one (11f)

Rf 0.65 (19:1 DCM:MeOH); M.p. 182-184° C.; IR (cm-1) 3261, 3184, 2932, 2852, 2809, 2358, 1670, 1621, 1593, 1539, 1509; 1H NMR (400 MHz, DMSO-d6) 1.50-1.57 (2H, m, N(CH2CH2CH)2), 1.60-1.67 (4H, m, N(CH2CH2CH)2), 3.07-3.13 (4H, m, N(CH2CH2CH)2), 4.66 (2H, dapp, J=5.9 Hz, N2-CH2), 4.88 (1H, dapp, J=17.2 Hz, allyl C-Htrans), 5.01 (1H, dapp, J=10.3 Hz, allyl C-Hcis), 5.71 (1H, ddt, J=17.2, 10.3, 5.9 Hz, allyl C—H), 6.95 (2H, d, J=8.3 Hz, H-3"/5"), 7.54 (2H, d, J=8.3 Hz, H-2"/6"), 7.85 (1H, dapp, J=7.7 Hz, H-5'), 8.22-8.30 (1H, m, H-3'), 8.31-8.38 (1H, m, H-4'), 8.87 (1H, s, H-4), 10.27 (1H, br, C6-NH); 13C NMR (125 MHz, DMSO-d6) 24.3 (piperidine-CH2), 25.8 (piperidine-CH2), 48.0 (N2-CH2), 50.5 (piperidine-CH2), 116.5, 118.4, 119.2, 121.3, 121.7 (q, JCF=273.5 Hz, CF3), 122.0, 130.6, 132.4, 141.2, 145.1 (q, JCF=34.2 Hz, Ar—C), 148.6, 149.3, 156.8, 161.5, 161.7, 162.4; MS [M+H]+m/z 496.3.

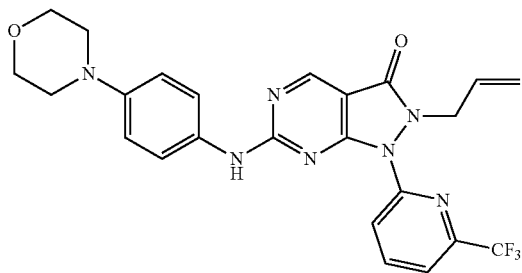 [SMILES: C=CCn1c(=O)c2cnc(Nc3ccc(N4CCOCC4)cc3)nc2n1-c1cccc(C(F)(F)F)n1]

2-Allyl-6-((4-morpholinophenyl)amino)-1-(6-(trifluoromethyl)pyridin-2-yl)-1,2-dihydro-3Hpyrazolo[3,4-d]pyrimidin-3-one (11g)

Rf 0.51 (19:1 DCM:MeOH); M.p. 215-217° C.; IR (cm-1) 3246, 3183, 3080, 2958, 2854, 2359, 1685, 1619, 1594, 1511; 1H NMR (400 MHz, DMSO-d6) 3.07-3.12 (4H, m, N(CH2CH2)2O), 3.73-3.78 (4H, m, N(CH2CH2)2O), 4.66 (2H, dapp, J=6.5 Hz, N2-CH2), 4.88 (1H, dapp, J=40 17.1 Hz, allyl C-Htrans), 5.01 (1H, dapp, J=10.4 Hz, allyl C-Hcis), 5.71 (1H, ddt, J=17.1, 10.4, 6.5 Hz, allyl CH), 6.97 (2H, d, J=8.3 Hz, H-3"/5"), 7.58 (2H, d, J=8.3 Hz, H-2"/6"), 7.86 (1H, dapp, J=8.1 Hz, H-5'), 8.24-8.38 (2H, m, H-3'/4'), 8.88 (1H, s, H-4), 10.29 (1H, br, C6-NH); 13C NMR (125 MHz, DMSO-d6) 48.0 (N2-CH2), 49.3 (N(CH2CH2)2O), 66.6 (N(CH2CH2)2O), 115.7, 118.4, 119.2, 121.3, 121.6 (q, JCF=274.3 Hz, CF3), 122.1, 131.3, 132.4, 141.2, 145.1 (q, JCF=34.9 Hz), 147.9, 149.4, 156.8, 161.5, 161.7, 162.4; MS [M+H]+m/z 498.3.

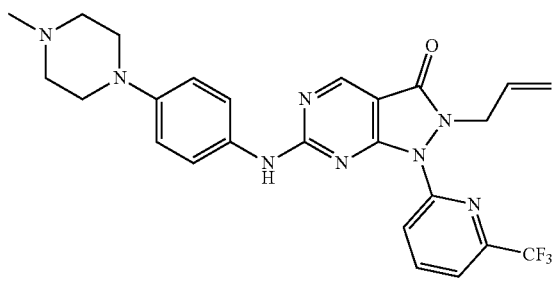 [SMILES: C=CCn1c(=O)c2cnc(Nc3ccc(N4CCN(C)CC4)cc3)nc2n1-c1cccc(C(F)(F)F)n1]

2-Allyl-6-((4-(4-methylpiperazin-1-yl)phenyl)amino)-1-(6-(trifluoromethyl)pyridin-2-yl)-1,2-dihydro-3H-pyrazolo[3,4-d]pyrimidin-3-one (11h)

Rf 0.39 (9:1 DCM:MeOH); M.p. 176-180° C.; IR (cm-1) 3261, 3185, 3086, 2926, 2837, 2792, 2343, 1671, 1622, 1540, 1510; 1H NMR (400 MHz, DMSO-d6) 2.23 (3H, s, NCH3), 2.45-2.49 (4H, m, N—(CH2CH2)2-NMe), 3.09-3.14 (4H, m, N—(CH2CH2)2-NMe), 4.66 (2H, dapp, J=6.3 Hz, N2-CH2), 4.88 (1H, dapp, J=16.8 Hz, allyl C-Htrans), 5.01 (1H, dapp, J=10.4 Hz, allyl C-Hcis), 5.71 (1H, ddt, J=16.8, 10.4, 6.3 Hz, allyl C—H), 6.96 (2H, d, J=8.5 Hz, H-3"/5"), 7.56 (2H, d, J=8.5 Hz, H-2"/6"), 7.85 (1H, dapp, J=7.5 Hz, H-5'), 8.24-8.40 (2H, m, H-3'/4'), 8.87 (1H, s, H-4), 10.27 (1H, br, C6-NH); 13C NMR (125 MHz, DMSO-d6) 46.2 (N—CH3), 48.0 (N2-CH2), 48.9 (piperazine-CH2), 55.1 (piperazine-CH2), 115.9, 118.4, 119.2, 121.3, 121.7 (q, JCF=274.3 Hz, CF3), 121.9, 123.0, 130.9, 132.5, 141.2, 145.1 (q, JCF=35.0 Hz, Ar—C), 147.9, 149.3, 156.8, 161.5, 161.7, 162.4; MS [M+H]+m/z 511.3.

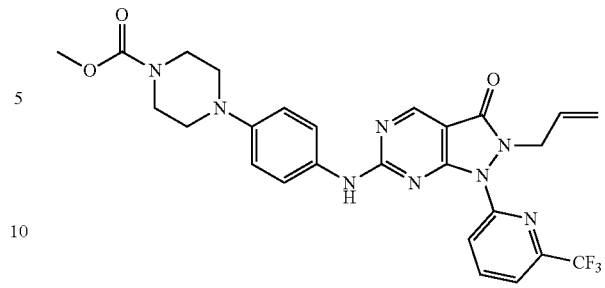

Methyl 4-(4-((2-allyl-3-oxo-1-(6-(trifluoromethyl)pyridin-2-yl)-2,3-dihydro-1H-pyrazolo[3,4-d]pyrimidin-6-yl)amino)phenyl)piperazine-1-carboxylate (11i)

Rf 0.61 (19:1 DCM:MeOH); M.p. 164-167 41° C.; IR (cm-1) 3256, 3080, 2954, 2918, 2849, 2358, 1683, 1608, 1569, 1538, 1511; 1H NMR (400 MHz, DMSO-d6) 3.07-3.12 (4H, m, N(CH2CH2)2NCO), 3.50-3.55 (4H, m, N(CH2CH2)2NCO), 3.64 (3H, s, CO2CH3), 4.66 (2H, dapp, J=5.9 Hz, N2-CH2), 4.88 (1H, dapp, J=17.0 Hz, allyl C-Htrans), 5.01 (1H, dapp, J=10.1 Hz, allyl C-Hcis), 5.71 (1H, ddt, J=17.0, 10.1, 5.9 Hz, allyl C—H), 6.99 (2H, d, J=8.1 Hz, H-3"/5"), 7.58 (2H, d, J=8.1 Hz, H-2"/6"), 7.86 (1H, dapp, J=7.5 Hz, H-5'), 8.24-8.31 (1H, m, H-3'), 8.32-8.39 (1H, m, H-4'), 8.88 (1H, s, H-4), 10.30 (1H, br, C6-NH); 13C NMR (125 MHz, DMSO-d6) 43.8 (piperazine-CH2), 48.0 (N2-CH2), 49.3 (piperazine-CH2), 52.9 (OCH3), 116.7, 118.4, 119.2, 121.3, 121.7 (q, JCF=274.2 Hz, CF3), 122.0, 131.6, 132.5, 141.2, 145.2 (q, JCF=34.7 Hz, Ar—C), 147.7, 149.3, 155.5, 156.8, 161.5, 161.7, 162.3; MS [M+H]+m/z 555.3.

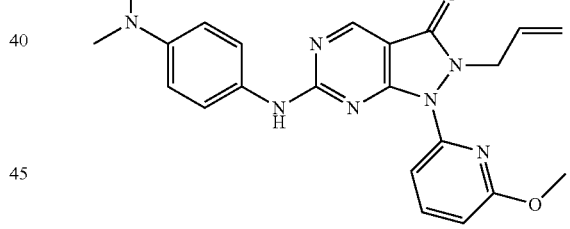

2-Allyl-6-((4-(dimethylamino)phenyl)amino)-1-(6-methoxypyridin-2-yl)-1,2-dihydro-3H-pyrazolo[3,4-d]pyrimidin-3-one (11j)

Rf 0.67 (19:1 DCM:MeOH); M.p. 126-128° C.; IR (cm-1) 3245, 3170, 2990, 2797, 2358, 1674, 1613, 1568, 1542, 1518; 1H NMR (400 MHz, DMSO-d6) 2.88 (6H, s, N(CH3)2), 3.89 (3H, s, —OCH3), 4.63-4.68 (2H, m, N2-CH2), 4.94 (1H, dapp, J=17.1 Hz, alkene C-Htrans), 5.04 (1H, dapp, J=10.4 Hz, alkene C-Hcis), 5.69 (1H, ddt, J=17.1, 10.4, 6.0 Hz, alkene C—H), 6.72 (2H, d, J=8.4 Hz, H-3"/5"), 6.79 (1H, dapp, J=8.2 Hz, H-4'), 7.46 (2H, d, J=8.4 Hz, H-2'/6'), 7.51-7.59 (1H, m, H-3'), 7.95 (1H, dd, J=7.6, 7.5 Hz, H-4'), 8.81 (1H, s, H-4), 10.09 (1H, br, C6-NH); 13C NMR (125 MHz, DMSO-d6) 41.0 (N(CH3)2), 47.4 (N2-CH2), 54.1 (OCH3), 108.1, 113.0, 118.8, 122.0, 129.1, 132.6, 141.5, 147.1, 147.5, 156.4, 161.6, 162.0, 163.2; MS [M+H]+m/z 418.2.

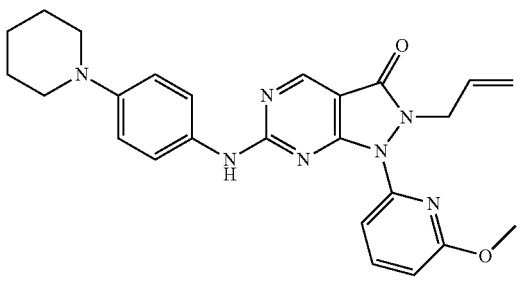 [SMILES: C=CCn1c(=O)c2cnc(Nc3ccc(N4CCCCC4)cc3)nc2n1-c1cccc(OC)n1]

2-Allyl-1-(6-methoxypyridin-2-yl)-6-((4-(piperidin-1-yl)phenyl)amino)-1,2-dihydro-3H-pyrazolo[3,4-d]pyrimidin-3-one (11k)

Rf 0.66 (19:1 DCM:MeOH); M.p. 166-167° C.; IR (cm-1) 3264, 3179, 3067, 2929, 2851, 2810, 2359, 1672, 1607, 1566, 1537, 1509; 1H NMR (400 MHz, DMSO-d6) 1.49-1.56 (2H, m, N(CH2CH2CH)2), 1.59-1.66 (4H, m, N(CH2CH2CH)2), 3.05-3.11 (4H, m, N(CH2CH2CH)2), 3.89 (3H, s, OCH3), 4.64-4.68 (2H, m, N2-CH2), 4.93 (1H, dapp, J=17.0 Hz, allyl C-Htrans), 5.04 (1H, dapp, J=10.4 Hz, allyl C-Hcis), 5.70 (1H, ddt, J=17.0, 10.4, 5.9 Hz, allyl C—H), 6.80 (1H, dapp, J=8.1 Hz, H-5'), 6.90 (2H, d, J=8.6 Hz, H-3"/5"), 7.43-7.48 (1H, m, H-3'), 7.54-7.61 (2H, m, H-2"/6"), 7.94-8.01 (1H, m, H-4'), 8.82 (1H, s, H-4), 10.15 (1H, br, C6-NH); 13C NMR (125 MHz, DMSO-d6) 24.3 (piperadine-CH2), 25.8 (piperadine-CH2), 47.4 (N2-CH2), 50.6 (piperadine-CH2), 54.1 (OCH3), 108.3, 116.5, 118.8, 121.6, 131.0, 132.6, 141.5, 147.0, 148.4, 156.4, 161.5, 161.9, 163.3; MS [M+H]+m/z 458.3.

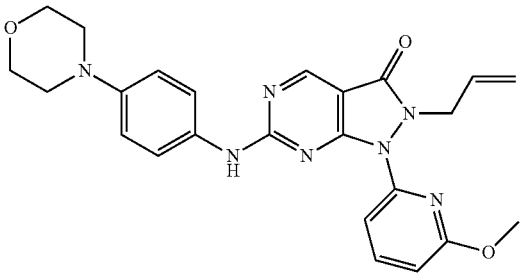 [SMILES: C=CCn1c(=O)c2cnc(Nc3ccc(N4CCOCC4)cc3)nc2n1-c1cccc(OC)n1]

2-Allyl-1-(6-methoxypyridin-2-yl)-6-((4-morpholinophenyl)thio)-1,2-dihydro-3H-pyrazolo[3,4-d]pyrimidin-3-one (11l)

Rf 0.55 (19:1 DCM:MeOH); M.p. 190-192° C.; IR (cm-1) 3272, 3185, 3082, 2977, 2947, 2848, 2360, 1686, 1603, 1567, 1540, 1510; 1H NMR (400 MHz, CDCl3) 3.19-3.24 (4H, m, N—(CH2CH2)2O), 3.88-3.92 (4H, m, N—(CH2CH2)2O), 3.97 (3H, s, —OCH3), 4.82 (2H, dapp, J=6.3 Hz, N2-CH2), 5.00 (1H, dd, J=17.1, 1.3 Hz, alkene C-Htrans), 5.07 (1H, dd, J=10.2, 1.3 Hz, alkene C-Hcis), 5.73 (1H, ddt, J=17.1, 10.2, 6.3 Hz, alkene C—H), 6.70 (1H, dd, J=8.1, 0.5 Hz, H-4'), 6.92 (2H, d, J=9.1 Hz, H-3"/5"), 7.41 (1H, dd, J=7.6, 0.4 Hz, H-3'), 7.51 (2H, d, J=9.1 Hz, H-2'/6'), 7.74 (1H, dd, J=8.1, 7.6 Hz, H-4'), 8.84 (1H, s, H-4); 13C NMR (125 MHz, DMSO-d6) 47.3 (N2-CH2), 49.4 (N(CH2CH2)2O), 54.1 (OCH3), 66.6 (N(CH2CH2 2O), 108.3, 115.7, 118.8, 121.6, 131.6, 132.6, 141.5, 147.0, 147.6, 156.5, 161.5, 161.9, 163.3; MS [M+H]+m/z 460.3.

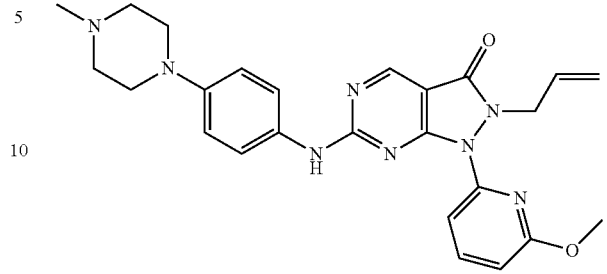

2-Allyl-1-(6-methoxypyridin-2-yl)-6-((4-(4-methylpiperazin-1-yl)phenyl)thio)-1,2-dihydro-3Hpyrazolo[3,4-d]pyrimidin-3-one (11m)

Rf 0.40 (9:1 DCM:MeOH); M.p. 72-76° C.; IR (cm-1) 3255, 3181, 3065, 2929, 2821, 2796, 2359, 1692, 1670, 1610, 1538, 1510; 1H NMR (400 MHz, CDCl3) 2.39 (3H, s, NCH3), 2.60-2.65 (4H, m, N—(CH2CH2)2-NMe), 3.19-3.24 (4H, m, N—(CH2CH2)2-NMe), 3.96 (3H, s, —OCH3), 4.81 (2H, dapp, J=6.3 Hz, N2-CH2), 5.00 (1H, dd, J=17.0, 1.4 Hz, alkene C-Htrans), 5.06 (1H, dd, J=10.2, 1.4 Hz, alkene C-Hcis), 5.73 (1H, ddt, J=17.0, 10.2, 6.3 Hz, alkene C—H), 6.69 (1H, dd, J=8.2, 0.4 Hz, H-4'), 6.93 (2H, d, J=9.0 Hz, H-3"/5"), 7.41 (1H, dd, J=7.7, 0.4 Hz, H-3'), 7.49 (2H, d, J=9.0 Hz, H-2'/6'), 7.74 (1H, dd, J=8.2, 7.7 Hz, H-4'), 8.84 (1H, s, H-4); 13C NMR (125 MHz, DMSO-d6) 46.2 (N—CH3), 47.4 (N2-CH2), 49.0 (piperazine-CH2), 54.1 (OCH3), 55.1 (piperazine-CH2), 108.2, 115.9, 118.8, 121.6, 131.3, 132.6, 141.5, 147.0, 147.6, 156.4, 161.5, 161.9, 163.3; MS [M+H]+m/z 473.3.

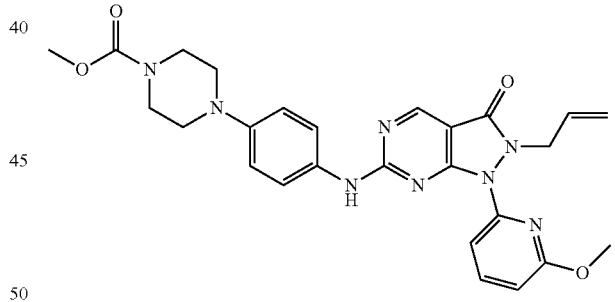

Methyl 4-(4-((2-allyl-1-(6-methoxypyridin-2-yl)-3-oxo-2,3-dihydro-1H-pyrazolo[3,4-d]pyrimidin-6-yl)amino)phenyl)piperazine-1-carboxylate (11n)

Rf 0.66 (19:1 DCM:MeOH); M.p. 197-200° C.; IR (cm-1) 3293, 3190, 2888, 2850, 2824, 2361, 1699, 1660, 1601, 1567, 1533, 1510; 1H NMR (400 MHz, DMSO-d6) 3.03-3.10 (4H, m, N(CH2CH2)2NCO), 3.48-3.55 (4H, m, N(CH2CH2)2NCO), 3.63 (3H, s, CO2CH3), 3.89 (3H, s, OCH3), 4.63-4.69 (2H, m, N2-CH2), 4.94 (1H, dapp, J=17.2 Hz, allyl C-Htrans), 5.04 (1H, dapp, J=10.3 Hz, allyl C-Hcis), 5.70 (1H, ddt, J=17.2, 10.3, 5.8 Hz, allyl C—H), 6.81 (1H, dapp, J=8.1 Hz, H-5'), 6.95 (2H, d, J=8.7 Hz, H-3"/5"), 7.45 (1H, dapp, J=7.3 Hz, H-3'), 7.56-7.65 (2H, m, H-2"/6"), 7.97 (1H, dd, J=7.5, 7.3 Hz, H-4'), 8.84 (1H, s, H-4), 10.18 (1H, br, C6-NH); 13C NMR (125 44 MHz, DMSO-d6) 43.8 (piperazine-CH2), 47.3 (N2-CH2), 49.4 (piperazine-CH2), 52.8 (CO2CH3), 54.1 (OCH3), 108.3, 110.8, 115.1, 116.8, 118.8, 119.2, 121.7, 132.0, 132.6, 141.5, 147.0, 147.4, 155.5, 156.5, 161.5, 161.8, 163.3; MS [M+H]+ m/z 517.3.

In view of the many possible embodiments to which the principles of the disclosed compounds, compositions and methods may be applied, it should be recognized that the illustrated embodiments are only preferred examples should not be taken as limiting the scope of the invention.

What is claimed is:

1. A compound, or a pharmaceutically acceptable salt thereof, selected from the group consisting of:

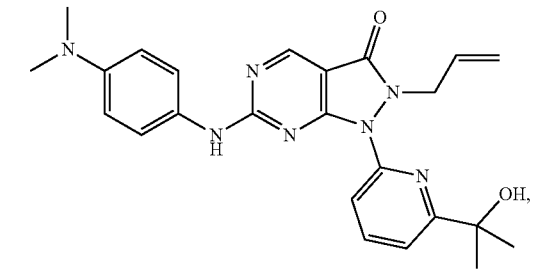

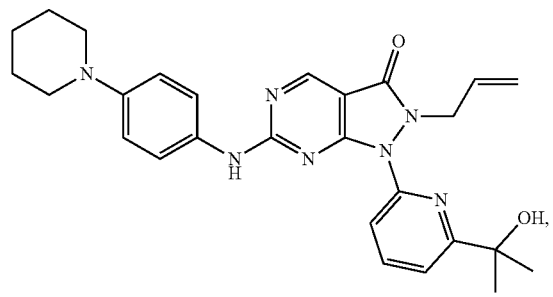

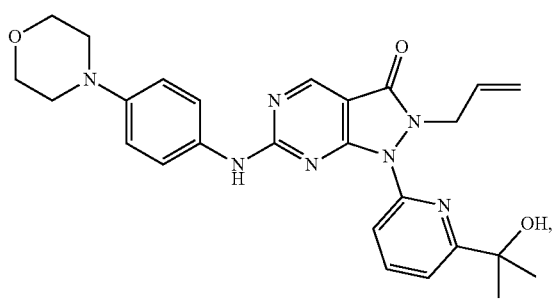

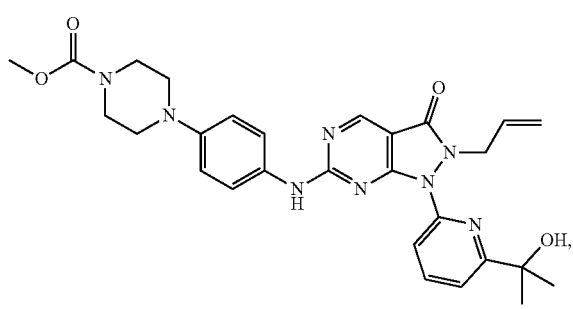

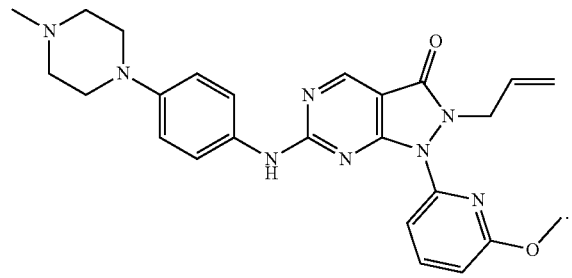

-continued
and

2. A pharmaceutical composition comprising a compound of claim 1, and at least one pharmaceutically acceptable additive.

3. A method of treating or ameliorating cancer in a subject, the method comprising administering a therapeutically effective amount of a compound of claim 1 to the subject, wherein the cancer is selected from medulloblastoma, primitive neuroectodermal tumors (PNET), pediatric glioblastoma multiforme (GBM), and pilocytic astrocytoma (PA).

4. The method of claim 3, wherein the compound is administered to the subject within a pharmaceutical composition.

5. The method of claim 4, wherein the pharmaceutical composition is a mono-phasic pharmaceutical composition suitable for parenteral or oral administration consisting essentially of a therapeutically effective amount of the compound, and a pharmaceutically acceptable additive.

6. The method of claim 4, wherein the pharmaceutical composition is administered with any one of cisplatin, capecitabine, carboplatin, cyclophosphamide, cytarabine, dauoribicin, docetaxel, doxorubicin, 5-fluorouracil, gemcitabine, methotrexate, paclitaxel, premetrexed, irinotecan temozolomide, topotecan, radiation, or combinations thereof.

7. The method of claim 4, wherein the pharmaceutical composition is administered in conjunction with at least one of cisplatin, cytarabine, or temozolomide.

8. The method of claim 3, wherein the cancer is medulloblastoma.

9. The compound of claim 1, or a pharmaceutically acceptable salt thereof, wherein the compound is:

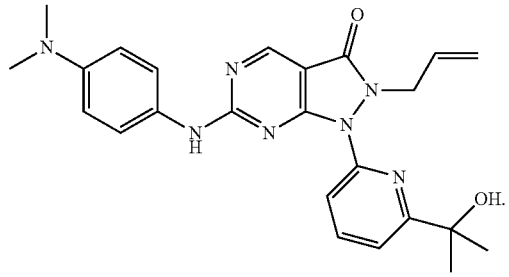 [SMILES: C=CCn1c(=O)c2cnc(Nc3ccc(N(C)C)cc3)nc2n1-c1cccc(C(C)(C)O)n1]

10. The compound of claim 1, or a pharmaceutically acceptable salt thereof, wherein the compound is:

11. The compound of claim 1, or a pharmaceutically acceptable salt thereof, wherein the compound is:
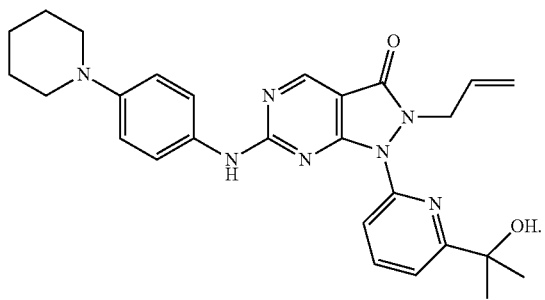 [SMILES: C=CCn1c(=O)c2cnc(Nc3ccc(N4CCCCC4)cc3)nc2n1-c1cccc(C(C)(C)O)n1]
12. The compound of claim 1, or a pharmaceutically acceptable salt thereof, wherein the compound is:
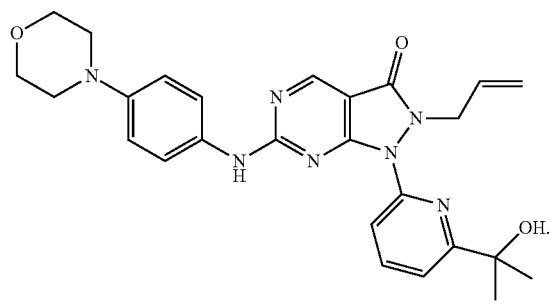 [SMILES: C=CCn1c(=O)c2cnc(Nc3ccc(N4CCOCC4)cc3)nc2n1-c1cccc(C(C)(C)O)n1]
13. The compound of claim 1, or a pharmaceutically acceptable salt thereof, wherein the compound is:
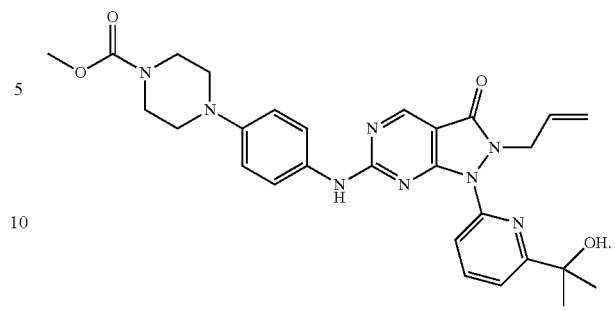
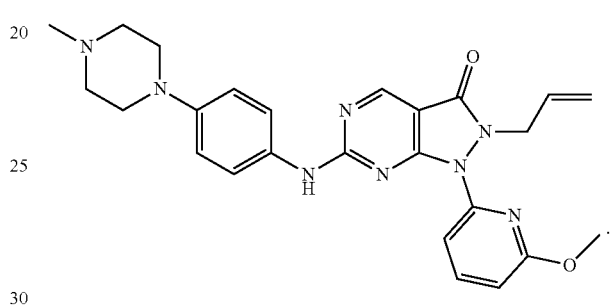
* * * * *

UNITED STATES PATENT AND TRADEMARK OFFICE
CERTIFICATE OF CORRECTION

Page 1 of 1

PATENT NO. : 10,947,238 B2
APPLICATION NO. : 15/772554
DATED : March 16, 2021
INVENTOR(S) : Philip Reigan et al.

It is certified that error appears in the above-identified patent and that said Letters Patent is hereby corrected as shown below:

On the Title Page

First column, (87) PCT Pub. No.:
"(87) PCT Pub. No.: WO2017/072629"
Should read:
-- (87) PCT Pub. No.: WO2017/075629 --

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*